(12) United States Patent
Yanagisawa

(10) Patent No.: US 8,871,794 B2
(45) Date of Patent: *Oct. 28, 2014

(54) SMALL-MOLECULE AGONISTS FOR TYPE-2 OREXIN RECEPTOR

(75) Inventor: Masashi Yanagisawa, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 46 days.

This patent is subject to a terminal disclaimer.

(21) Appl. No.: 13/590,064

(22) Filed: Aug. 20, 2012

(65) Prior Publication Data

US 2014/0051700 A1    Feb. 20, 2014

Related U.S. Application Data

(63) Continuation of application No. 12/478,753, filed on Jun. 4, 2009, now Pat. No. 8,258,163.

(60) Provisional application No. 61/058,914, filed on Jun. 4, 2008.

(51) Int. Cl.
*A61K 31/4168*    (2006.01)

(52) U.S. Cl.
USPC .......................................................... 514/388

(58) Field of Classification Search
None
See application file for complete search history.

(56) References Cited

U.S. PATENT DOCUMENTS 8,258,163 B2 *   9/2012   Yanagisawa ................. 514/388
2005/0228022 A1 *  10/2005  Drasner et al. ............... 514/320

* cited by examiner

*Primary Examiner* — Sreeni Padmanabhan
*Assistant Examiner* — Jody Karol
(74) *Attorney, Agent, or Firm* — Richard Aron Osman

(57) ABSTRACT

Methods and compositions for agonizing a type-2 orexin receptor (OX2R) in a cell determined to be in need thereof, including the general method of (a) administering to a subject a cyclic guanidinyl OX2R agonist and (b) detecting a resultant enhanced wakefulness or increased resistance to diet-induced accumulation of body fat, or abbreviated recovery from general anesthesia or jet lag.

31 Claims, 3 Drawing Sheets

SMALL-MOLECULE AGONISTS FOR TYPE-2 OREXIN RECEPTOR

This application claims priority to U.S. Ser. No. 61/058,914, filed Jun. 4, 2008, and having the same title and inventor.

The field of the invention is small-molecule agonists for type-2 orexin receptor

INTRODUCTION

This invention describes several chemically distinct classes of non-peptidic, small-molecule agonists for the type-2 orexin receptors (OX2R). Orexins are hypothalamic neuropeptides that are importantly implicated in sleep/wake control and body weight homeostasis. Orexin producing neurons are exclusively localized in the lateral hypothalamic area. The peptides act on two G protein-coupled receptors termed OX1R and OX2R. It has been demonstrated that deficiency in orexin/OX2R signaling causes the sleep disorder narcolepsy in humans, mice and dogs. Narcolepsy is a socially debilitating disorder characterized by an inability to properly maintain wakefulness (excessive daytime sleepiness, sleep attacks), and a pathological intrusion of signs of REM sleep into wakefulness (cataplexy, hipnagorgic hallucination, sleep paralysis, etc). Narcolepsy affects $1/1,000 \sim 1/2,000$ individuals, and is a non-progressive, life-long condition. A vast majority (>90%) of human narcoleptics lacks detectable levels of orexin peptides in the cerebrospinal fluid due to a highly specific (probably autoimmune) degeneration of orexin neurons, indicating that human narcolepsy is an "orexin deficiency syndrome."

A transgenic mouse strain that has been engineered to mimic the neurochemical situation in human narcoleptics, i.e., with a postnatal loss of orexin neurons, exhibits all symptoms of narcolepsy/cataplexy. It has been further demonstrated that these mice can then be effectively treated for narcolepsy by providing exogenous orexin either genetically (via a transgene) or pharmacologically (via intracerebroventricular injections). Hence, orexin replacement therapy is expected to provide similarly effectively treat human narcolepsy patients.

Orexins themselves are peptides (thus orally inactive) and blood-brain barrier impermeable; they cannot be used as an orally active therapeutic agent. However, if we can develop an orally active, blood-brain barrier permeable, small-molecule OX2R agonist, such compound will be useful as a drug for the treatment of narcolepsy.

This invention provides a cellular assay method that can be used for high-throughput screening of OX2R agonists from chemical compound libraries. The screen method uses transfected cell lines co-expressing the human OX2R cDNA (or another control receptor cDNA) and an NFAT-responsive luciferase reporter. Furthermore, the invention provides results from actual screenings utilizing this assay method, identifying several distinct classes of active compounds, which can be optionally further optimized chemically using the same assay.

The practical uses for OX2R agonists go beyond the treatment of narcolepsy. Since orexin has been established as an endogenous neurotransmitter to maintain proper wakefulness, orexin receptor agonists effect a highly "natural" form of wakefulness. Therefore, such agonists may be used to treat medical conditions accompanying daytime sleepiness, such as nighttime insomnia, and depression with hypersomnia.

It has also been shown that orexin/OX2R signaling acts as a net-negative regulator of body weight homeostasis. Thus, deficiencies in OX2R signaling can cause (besides narcolepsy) obesity in mice and humans, whereas transgenic OX2R over-activation renders mice resistant to high fat diet-induced obesity. Furthermore, intracerebroventricular infusion of a previously known peptidic OX2R-selective agonist similarly prevents high fat diet-induced obesity in mice. Therefore, orally active OX2R agonists also provide treatments of obesity and associated metabolic syndrome.

Orexin deficiency causes delayed recovery from gas anesthesia in mice, which effect can be antagonized by orexin and orexin agonists. See, Kelz et al. An essential role for orexins in emergence from general anesthesia. Proc. Natl. Acad. Sci. USA 105:1309-1314 (2008). Hence, the subject orexin agonists may also be used to facilitate or expedite recovery from general anesthesia.

The active OX2R agonists provided in this invention also provide lead compounds for the development of alternative and more potent forms with desirable pharmacokinetics, bioavailability, nontoxicity, and other properties. Such derivative compounds may be used, inter alia and after proper clinical trials, as therapeutic agents for treating (1) narcolepsy; (2) other neurologic conditions accompanying daytime sleepiness, such as night time insomnia and depression with hypersomnia, sleep apnea, jet lag, etc.; (3) obesity and metabolic syndrome; and (4) undesirable extension and lingering effects of general anesthesia.

The general class of OX2R agonists identified herein was independently described for use as local analgesics (see, WO 03/105779), and a preferred embodiment described herein has the same structure as compound #11 in Table 1 of WO 03/105779.

SUMMARY OF THE INVENTION

The invention provides methods and compositions for agonizing a type-2 orexin receptor (OX2R) in a cell determined to be in need thereof. The general methods comprise the steps of (a) contacting the receptor with an OX2R agonist of formula I:

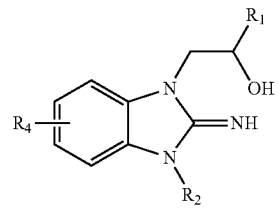

as further defined in various embodiments below, or a pharmaceutically acceptable salt thereof, or prodrug thereof; and (b) detecting a resultant agonizing or activation of the receptor.

In particular embodiments, the method provides a drug screen or optimization assay, wherein the cell is in vitro and further comprises a transcriptional reporter of OX2R activation, and the agonizing is detected as increased expression of the reporter.

In particular embodiments, the method provides a therapy or prophylaxis, wherein the cell is in situ in a subject, the OX2R agonist is orally administered to the subject, and the agonizing or activation is inferred from a resultant physiological effect, such as enhanced wakefulness or increased resistance to diet-induced accumulation of body fat, or enhanced recovery from general anesthesia or jet lag. In more specific embodiments, this in situ protocol comprises (i) administering to the subject the OX2R agonist regularly and chronically; (ii) administering to the subject the OX2R agonist in conjunction with an effective amount of a different compound which promotes wakefulness, anti-obesity, or recovery from general anesthesia or jet lag; or (iii) administering to the subject the OX2R agonist in unit dosage form, and comprising the antecedent step of removing a capsule or tablet comprising the unit dosage form from a multipack adapted for sequential use.

The invention also provides pharmaceutical compositions comprising an OX2R agonist of formula I (as defined in various embodiments below), particularly as coformulated with a different compound which promotes wakefulness, anti-obesity, or recovery from general anesthesia or jet lag, and/or formulated in unit dosages separately packaged in a multipack adapted for sequential use.

DEFINITIONS

Figure 1:
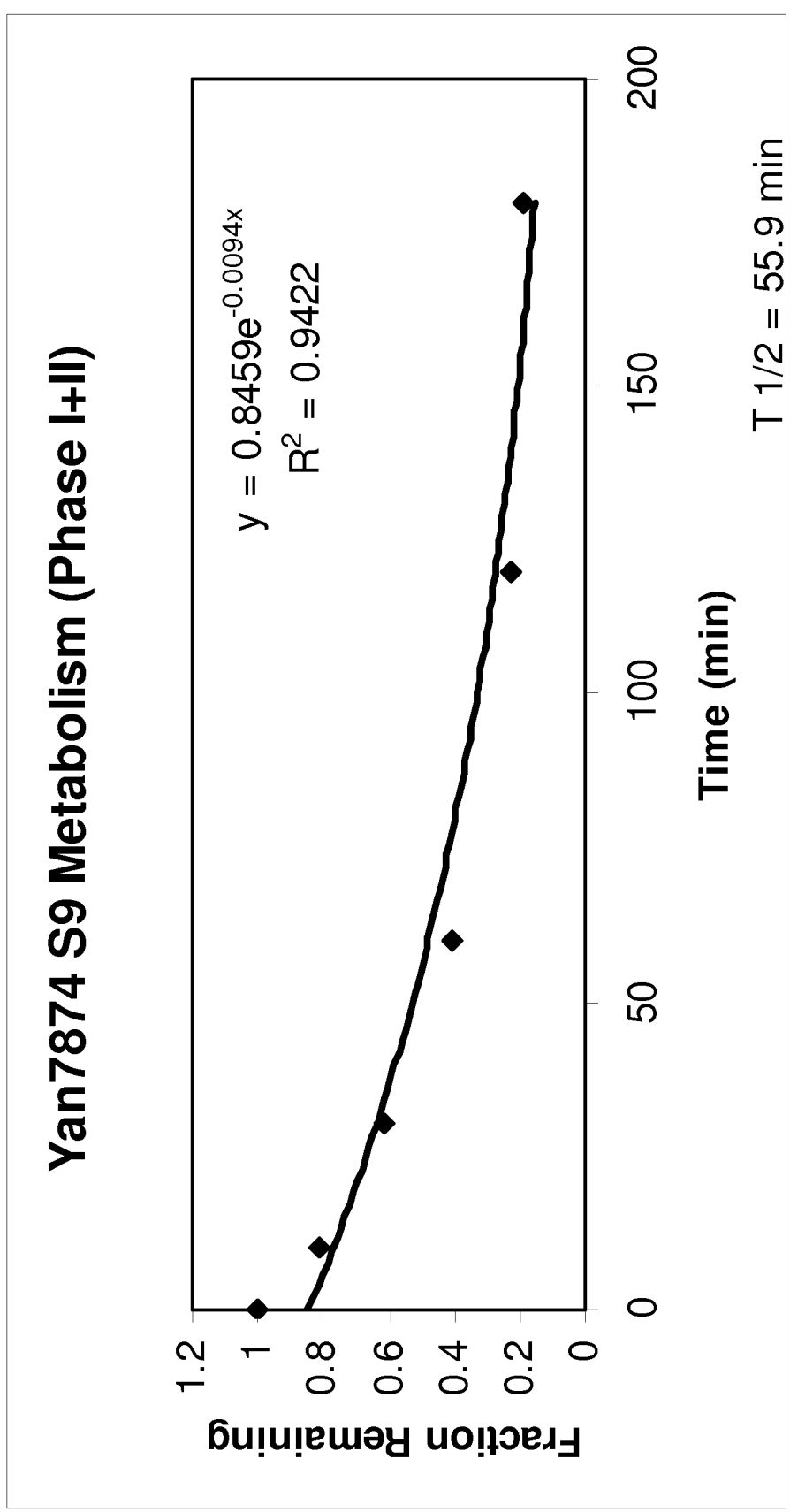
FIG. 1. Yan 7874: Metabolism Studies
FIG. 2. Yan 7874: Pharmacokinetics Studies
FIG. 3. Yan 7874: SAR Studies around the cyclic guanidinium scaffold.

As used herein, terms have the following meanings:

Alkyl, alkoxy, alkoxyalkyl, alkylthio: saturated acyclic moieties, with straight or branched chains, having the indicated number of carbon atoms. Alkyl groups are hydrocarbyl moieties; alkoxy and alkoxyalkyl groups have an oxygen atom in the chain; alkylthio groups have a sulfur atom in the chain. Examples include methyl, ethyl, and the various propyl, butyl, pentyl, hexyl and octyl groups, methoxy, ethoxy, n-propoxy, isopropoxy, methoxymethyl, ethoxymethyl, n-propoxyethyl, methylthio, ethylthio, n-propylthio and n-butylthio.

Alkyleneoxy; alkylenedioxy: includes methylenedioxy, —OCH$_2$O—, ethylenedioxy, —OCH$_2$CH$_2$O— and ethyleneoxy, —CH$_2$CH$_2$O—.

Cycloalkyl: saturated cyclic hydrocarbyl moieties, analogous to alkyl groups, having the indicated number of carbon atoms. Examples include cyclopropyl, cyclobutyl, cyclopentyl, cyclohexyl, cycloheptyl and cylooctyl.

Alkenyl: Unsaturated acyclic hydrocarbyl moieties, with straight or branched chains, containing one or more double (olefinic) bonds, and having the indicated number of carbon atoms. Examples include vinyl, allyl, isopropenyl, 2-butenyl, 1,3-butadienyl, and the various pentenyl, hexenyl and octenyl groups.

Alkyl, alkenyl cycloalkyl and other aliphatic groups may be unsubstituted or may be substituted. Typical substituents include halo, hydroxy, cyano, nitro, COOH and COOCH$_3$. Substituted moieties may have from one to as many substituents as are possible on the group in question. Preferably, substituted alkyl, alkenyl and cycloalkyl moieties have from 1 to 4 substituents (of course, with a maximum number of substituents possible for the group in question). In polysubstituted compounds the substituents may be the same or different, i.e. an alkyl group may be substituted with two or three different halogens, or with halo and hydroxyl groups.

Aralkyl: as generally used, refers to an alkyl group having an aryl substituent. Aralkyl groups in compounds of the present invention and their compositions and uses have the general formula (CH$_2$)$_{1-4}$Ph$_{1-2}$ where Ph stands for phenyl. That is, they have from 1 to 4 methylene groups in a chain, substituted by one or two phenyl groups. An example of such an aralkyl group is 3,3-diphenylpropyl.

Halo includes fluoro, chloro, bromo and iodo substituents as indicated. Where a moiety or compound includes multiple halogens, they may be the same or different; i.e. such a compound or moiety may contain two or more different halogen atoms.

Fused carbocyclic ring moieties include fully or partly unsaturated rings such as naphthyl, tetrahydronapthyl and phenyl substituted by alkylene groups having 2-4 carbon atoms. One example of the last-mentioned type of fused ring is indanyl, i.e. a phenyl ring substituted with a propylene (—CH$_2$CH$_2$CH$_2$—) moiety.

Heterocyclic moieties include both saturated and unsaturated cyclical moieties having the indicated number of members, or atoms, including one or more nitrogen, sulfur and/or oxygen atoms, as indicated. The remaining atoms in the ring are carbon atoms. The moieties may contain the atoms in a single ring or in a fused ring. Examples of five-membered heterocyclic rings include thienyl, furyl, tetrahydrofuryl, oxazolyl, isoxazolyl, thiazolyl, isothiazolyl, thiazolidinyl, pyrrolyl, pyrrolidinyl, pyrrolinyl, imidazolyl, imidazolidinyl, pyrazolyl, triazolyl, and pyrazolidinyl. Examples of six-membered heterocyclic rings include pyridyl, pyrazinyl, pyrimidinyl, triazinyl, piperidyl, morpholinyl, pyranyl, tetrahydropyranyl, and piperazinyl.

Examples of heterocyclic moieties having more than six carbons include indolyl, quinuclidyl, quinolyl, chromanyl, benzimidazolyl, benzoxazolyl, benzothienyl, benzofuranyl, and quinolinyl.

Heterocyclic moieties may be unsubstituted or may be substituted, for instance, by from 1 to 3 groups independently selected from halo, C$_1$-C$_4$ alkyl, hydroxy, or oxo, including combinations of such substituents.

Unsaturated moieties include in the case of carbocyclic and heterocyclic rings partially unsaturated moieties such as 1,2, 3,4-tetrahydropyndinyl and 2,3-dihydroindolyl, and fully unsaturated moieties such as pyridinyl and indolyl.

DESCRIPTION OF PARTICULAR EMBODIMENTS OF THE INVENTION

The general methods comprise the steps of contacting the receptor with an OX2R agonist of formula I, and detecting a resultant agonizing or activation of the receptor. The contacting is generally effected by administering to a person an effective amount of one or more compounds having the general formula I:

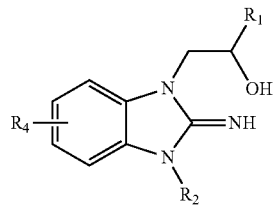

in which:
R$_1$, is
substituted or unsubstituted alkyl;
substituted or unsubstituted cycloalkyl;
substituted or unsubstituted alkenyl;
adamantyl;
substituted or unsubstituted phenyl;
a 5- or 6-membered optionally substituted saturated or unsaturated heterocyclic group having from one to three heteroatoms selected from nitrogen, oxygen and sulfur;

substituted or unsubstituted benzyl;

a saturated or unsaturated fused ring carbocyclic group having from 8 to 10 ring atoms; or (i)$CH_2XR_5$, where X is oxygen, sulfur, —NH— or —$CH_2$— and $R_5$ is substituted or unsubstituted alkyl; substituted or unsubstituted cycloalkyl; substituted or unsubstituted phenyl; substituted or unsubstituted benzyl; 2-carbamide-indolyl; or a 5 to 9-membered optionally substituted saturated or unsaturated heterocyclic group having from one to three heteroatoms selected from nitrogen, oxygen and sulfur;

$R_2$ is substituted or unsubstituted alkyl;

substituted or unsubstituted cycloalkyl;

substituted or unsubstituted alkenyl;

substituted or unsubstituted alkoxyalkyl;

a 5- or 6-membered optionally substituted saturated or unsaturated heterocyclic group having from one to three heteroatoms selected from nitrogen, oxygen and sulfur;

—$(CH_2)_nR_3$, where $R_3$ is (i) a 5- to 9-membered optionally substituted saturated or unsaturated heterocyclic group having from one to three heteroatoms selected from nitrogen, oxygen and sulfur; (ii) —$NR_6R_7$ where $R_6$ and $R_7$ are independently selected from hydrogen, methyl, ethyl and benzyl; or (iii) $COOR_8$ where $R_8$ is alkyl; and n is 2 or 3;

substituted or unsubstituted phenyl;

substituted or unsubstituted benzyl;

a saturated or unsaturated fused ring carbocyclic group having from 8 to 10 ring atoms; or methylene-1-naphthyl; and $R_4$ is hydrogen;

$(CH_2)_mCOOR_{15}$ where $R_{15}$ is alkyl or substituted alkyl; and m is 0, 1 or 2;

$CONR_{16}R_{17}$, where $R_{16}$ and $R_{17}$ are independently (i) hydrogen; (ii) alkyl or substituted alkyl; (iii) cycloalkyl; (iv) alkoxyalkyl; (v) a 5- to 10-membered optionally substituted saturated or unsaturated heterocyclic group having from one to three heteroatoms selected from nitrogen, oxygen and sulfur; (vi) a saturated or unsaturated fused ring carbocyclic group having from 8 to 10 ring atoms; (vii) substituted or unsubstituted phenyl; (viii) $(CH_2)_pR18$ where $R_{18}$ is a 5- or 6-membered optionally substituted saturated or unsaturated heterocyclic group having from one to three heteroatoms selected from nitrogen, oxygen and sulfur, and p is 1, 2 or 3; (ix) optionally substituted benzyl; or (x) an aralkyl group comprising a chain of from 1 to 4 methylene groups substituted by one or two phenyl groups;

$C_1$-$C_4$ alkoxy;

optionally substituted phenoxy;

$SO_2NR_{19}R_{20}$ where $R_{19}$ and $R_{20}$ are independently hydrogen, optionally substituted alkyl or phenyl;

$NR_{21}R_{22}$;

$COR_{23}$ where $R_{23}$ is alkyl or is $NR_{21}R_{22}$; (j) $COOR_{23}$ where $R_{23}$ is hydrogen, alkyl, or benzyl; or $SO_2R_{25}$ where $R_{25}$ is alkyl or $NR_{21}R_{22}$; wherein $R_{21}$ and $R_{22}$ are independently hydrogen, alkyl, optionally substituted phenyl or optionally substituted benzyl;

or a pharmaceutically acceptable salt thereof, or a prodrug thereof.

In another embodiment the OX2R agonist is of the same general formula I (supra) in which:

$R_1$ is $C_1$-$C_6$ alkyl, optionally substituted with one or more groups selected from halo, hydroxy, cyano, nitro, COOH and $COOCH_3$;

$C_2$-$C_6$ alkenyl, optionally substituted with one or more groups selected from halo, hydroxy, cyano, nitro, COOH and $COOCH_3$;

$C_3$-$C_6$ cycloalkyl, optionally substituted with one or more groups selected from halo, hydroxy, cyano, nitro, COOH and $COOCH_3$;

adamantyl;

optionally substituted phenyl in which the substituents are selected from mono and dihalo, mono- and di-($C_1$-$C_4$ alkoxy), mono- and di-($C_1$-$C_4$ alkylthio), $C_1$-$C_2$ alkyleneoxy; $C_1$-$C_2$ alkylenedioxy, mono- and di-($C_1$-$C_4$ alkyl), mono- and di-(trifluoromethyl), mono- and di-($C_1$-$C_4$ hydroxyalkyl), mono- and di-($C_1$-$C_4$ alkoxyalkyl), mono- and di-hydroxy, mono- and di-cyano, mono- and di-($COCH_3$), and mono- and di-$NHR_{26}$, wherein $R_{26}$ is $COCH_3$, $SO_2CH_3$, $SO_2C_6H_5$, COOR' or CONR'R"; and wherein R' and R" are independently hydrogen or $C_1$-$C_4$ alkyl;

a 5- or 6-membered saturated or unsaturated heterocyclic group having from one to three heteroatoms selected from nitrogen, oxygen and sulfur, optionally substituted by from 1 to 3 groups independently selected from halo, $C_1$-$C_4$ alkyl, $C_1$-$C_4$ alkoxy, oxo and hydroxy;

optionally substituted benzyl in which the substituents are selected from mono- and dihalo, mono- and di-($C_1$-$C_4$ alkoxy), mono- and di-($C_1$-$C_4$ alkylthio), $C_1$-$C_2$ alkyleneoxy; $C_1$-$C_2$ alkylenedioxy, mono- and di-($C_1$-$C_4$ alkyl), mono- and di-(trifluoromethyl), mono- and di-($C_1$-$C_4$ hydroxyalkyl), mono- and di-($C_1$-$C_4$ alkoxyalkyl), mono- and di-hydroxy, mono- and di-cyano, mono- and di-($COCH_3$), and mono- and di-$NHR_{26}$;

naphthyl; or $CH_2XR_5$, where X is oxygen, sulfur, —NH— or —$CH_2$— and $R_5$ is selected from (i) $C_1$-$C_6$ alkyl; (ii) $C_3$-$C_6$ cycloalkyl; (iii) optionally substituted phenyl in which the substituents are selected from mono- and di-($C_1$-$C_4$ alkyl), mono- and dihalo, mono and di-($C_1$-$C_4$ alkoxy), $C_1$-$C_2$ alkyleneoxy, $C_1$-$C_2$ alkylenedioxy, mono- and di-(trifluoromethyl), nitro, hydroxy, mono- and di-($C_1$-$C_4$ hydroxyalkyl), mono- and di-($C_1$-$C_4$ alkoxyalkyl), mono- and di-hydroxy, mono- and dicyano, mono- and di-($COCH_3$) and mono- and di-$NHR_{26}$; (iv) benzyl; (v) 2-carbamide-indolyl; or (vi) a 5- to 9-membered saturated or unsaturated heterocyclic group having from one to three heteroatoms selected from nitrogen, oxygen and sulfur, optionally substituted by from 1 to 3 groups independently selected from halo, $C_1$-$C_4$ alkyl, $C_1$-$C_4$ alkoxy, oxo and hydroxy;

$R_2$ is $C_1$-$C_{12}$ alkyl, optionally substituted with one or more groups selected from halo, hydroxy, cyano, nitro, COOH and $COOCH_3$;

$C_2$-$C_8$ cycloalkyl, optionally substituted with one or more groups selected from halo, hydroxy, cyano, nitro, COOH and $COOCH_3$;

$C_2$-$C_{12}$ alkenyl, optionally substituted with one or more groups selected from halo, hydroxy, cyano, nitro, COOH and $COOCH_3$;

$C_2$-$C_{12}$ alkoxyalkyl;

a 5- or 6-membered saturated or unsaturated heterocyclic group having from one to three heteroatoms selected from nitrogen, oxygen and sulfur, optionally substituted by from 1 to 3 groups independently selected from halo, $C_1$-$C_4$ alkyl, $C_1$-$C_4$alkoxy, oxo, and hydroxy;

—$(CH_2)nR_3$, where $R_3$ is (i) a 5- to 9-membered saturated or unsaturated heterocyclic group having from one to three heteroatoms selected from nitrogen, oxygen and sulfur, optionally substituted by from 1 to 3 groups independently selected from halo, $C_1$-$C_4$ alkyl, $C_1$-$C_4$ alkoxy, oxo, and hydroxy; (ii) —$NR_6R_7$ where $R_6$ and $R_7$ are independently selected from hydrogen, methyl, ethyl and benzyl; or (iii) $COOR_8$ where $R_8$ is $C_1$-$C_4$ alkyl; and n is 2 or 3;

optionally substituted phenyl, where the substituents are independently selected from mono- and di-($C_1$-$C_4$ alkyl); mono- and dihalo; mono-, di-, and tri-($C_1$-$C_4$ alkoxy); mono- and dicyano; nitro; methylsulfonyl; mono-, di-, and tri-(trifluoromethyl); $C_1$-$C_2$ alkyleneoxy; $C_1$-$C_2$ alkylenedioxy; —$(CH_2)_qCOOR_9$ where $R_9$ is $C_1$-$C_4$ alkyl; or —$(CH_2)_qNR_{10}R_{11}$ where $R_{10}$ and $R_{11}$ are independently selected from hydrogen, $C_1$-$C_4$ alkyl, $COR_{12}$ where $R_{12}$ is $C_1$-$C_4$ alkyl, $SO_2R_{13}$ where $R_{13}$ is $C_1$-$C_4$ alkyl, or $COOR_{14}$ where $R_{14}$ is $C_1$-$C_4$ alkyl and CONR'R"; and q is an integer from 1 to 4;

optionally substituted benzyl, where the substituents are selected from mono-, di-, and tri-($C_1$-$C_4$) alkyl; mono-, di-, and tri-halo; mono-, di-, and tri-($C_1$-$C_4$ alkoxy); mono-, di-, and tri-($C_1$-$C_4$ alkylthio); mono- and di-cyano; nitro; methylsulfonyl; mono-, di-, and tri-(trifluoromethyl); mono-, di-, and tri-COOR'; mono-, di-, and triCONR'R"; mono-, di-, and tri-$NR_{27}R_{28}$ where $R_{27}$ and $R_{28}$ are independently selected from hydrogen, C1-C4 alkyl, acetyl, and methylsulfonyl; $C_1$-$C_2$ alkyleneoxy; $C_1$-$C_2$ alkylenedioxy; and mono-, di-, and tri-($C_1$-$C_6$ alkoxyalkyl);

a saturated or unsaturated fused ring carbocyclic group having from 8 to 10 ring atoms; or methylene-1- or 2-naphthyl;

and $R_4$ is hydrogen;

$(CH_2)_m$COOR' where m is 0, 1 or 2;

$CONR_{16}R_{17}$ where $R_{16}$ and $R_{17}$ are independently (i) hydrogen; (ii) $C_1$-$C_5$ alkyl optionally substituted with one or more groups selected from halo, hydroxy, cyano, nitro, COOH and COOCH$_3$; (iii) $C_3$-$C_6$ cycloalkyl; (iv) $C_2$-$C_8$ alkoxyalkyl; (v) a 5- to 10-membered saturated or unsaturated heterocyclic group having from one to three heteroatoms selected from nitrogen, oxygen and sulfur, optionally substituted by from 1 to 3 groups independently selected from halo, hydroxy, oxo, $C_1$-$C_4$ alkyl, $C_1$-$C_4$ alkoxy, $COCH_3$, COOR', and $NR_{29}R_{30}$ where $R_{29}$ and $R_{30}$ are independently selected from hydrogen, $C_1$-$C_4$ alkyl, acetyl, or methylsulfonyl; (vi) a saturated or unsaturated fused ring carbocyclic group having from 8 to 10 ring atoms; (vii) $(CH_2)_pR_{18}$ where $R_{18}$ is a 5- or 6-membered saturated or unsaturated heterocyclic group having from 1 to 3 heteroatoms selected from nitrogen, oxygen and sulfur, optionally substituted by from 1 to 3 groups independently selected from halo, hydroxyl, $C_1$-$C_4$ alkyl, $C_1$-$C_4$ alkoxy and oxo, and p is 1,2 or 3; (viii) phenyl optionally substituted by one or more groups independently selected from mono-, di-, and tri-halo, mono-, di-, and trihydroxy, mono-, di-, and tri-($C_1$-$C_4$ alkyl), $C_1$-$C_2$ alkyleneoxy, $C_1$-$C_2$ alkylenedioxy, COOR', and $NR_{29}R_{30}$ where $R_{29}$ and $R_{30}$ are independently selected from hydrogen, $C_1$-$C_4$ alkyl, acetyl, and methylsulfonyl; (ix) optionally substituted benzyl where the substituents are selected from mono-, di-, and tri-($C_1$-$C_4$ alkyl); mono-, di-, and trihalo; mono-, di-, and tri-($C_1$-$C_4$ alkoxy); nitro; methylsulfonyl; mono-, di-, and tri-(trifluoromethyl); NR'R"; $C_1$-$C_2$ alkyleneoxy; $C_1$-$C_2$ alkylenedioxy; (x) an aralkyl group comprising a chain of from 1 to 4 methylene groups substituted by one or two phenyl groups;

$C_1$-$C_4$ alkoxy;

optionally substituted phenoxy, where the substituents are independently selected from mono- and di-($C_1$-$C_4$) alkyl; mono- and dihalo; mono-, di-, and tri- ($C_1$-$C_4$ alkoxy); cyano; nitro; methylsulfonyl; mono-, di-, and tri-trifluoromethyl; $C_1$-$C_4$ alkyleneoxy; $C_1$-$C_2$ alkylenedioxy; —$(CH_2)_rCOOR_9$ where $R_9$ is $C_1$-$C_4$ alkyl; or $(CH_2)_rNR_{30}R_{31}$, where $R_{30}$ and $R_{31}$ are independently hydrogen, $C_1$-$C_4$ alkyl, $COR_{32}$ where $R_{32}$ is $C_1$-$C_4$ alkyl, $SO_2R_{33}$ where $R_{33}$ is $C_1$-$C_4$ alkyl, or $COOR_{34}$ where $R_{34}$ is $C_1$-$C_4$ alkyl;

$SO_2NR_{35}R_{36}$ where $R_{35}$ and $R_{36}$ are independently hydrogen, $C_1$-$C_4$ alkyl or phenyl; or $NR_{37}R_{38}$ where $R_{37}$ and $R_{38}$ are independently hydrogen; $C_1$-$C_4$ alkyl; phenyl; $COR_{39}$ where $R_{39}$ is $C_1$-$C_4$ alkyl; or $SO_2R_{40}$ where $R_{40}$ is hydrogen or $C_1$-$C_4$ alkyl;

and pharmaceutically acceptable salts thereof, and prodrugs thereof.

More particular embodiments include those:

in which $R_1$ is phenyl, substituted phenyl (compounds in which $R_1$ is unsubstituted phenyl and mono— or dihalophenyl being especially preferred), heterocyclic groups (thienyl being especially preferred), or $CH_2XR_5$, (especially preferred are those compounds where X is oxygen and $R_5$ is substituted or unsubstituted phenyl or is benzyl);

in which $R_2$ is benzyl, substituted benzyl, $C_2$-$C_4$ alkyl, or —$(CH_2)_2R_3$, where $R_3$ is a 5- to 6-membered saturated or unsaturated heterocyclic group having from one to three heteroatoms selected from nitrogen, oxygen and sulfur (2-N-piperidoethyl being most preferred of these);

and in which $R_4$ is hydrogen;

or in which $R_1$, $R_2$ and $R_4$ are combinations of these preferred subgroups.

Table 1 below includes representative compounds of this series. As shown, the compounds in Table 1 are in the form of salts, particularly the hydrochloride and hydrobromide salts. However, this was done for convenience, and the invention is not limited to the use of these or other salts, but encompasses the compounds per se as well as their pharmaceutically acceptable salts.

TABLE 1

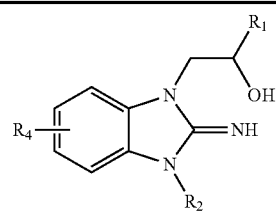

| Compound no./salt | R1 | R2 | R4 |
|---|---|---|---|
| 1 / hydrochloride | —CH$_2$O(4-ClC$_6$H$_4$) (4-chlorophenoxy-methyl) | benzyl | H |
| 2 / hydrochloride | 3,4-dichlorophenyl | benzyl | H |
| 3 / hydrochloride | —CH$_2$OC$_6$H$_5$(phenoxymethyl) | benzyl | H |
| 4 / hydrochloride | phenoxymethyl | 4-methylbenzyl | H |

TABLE 1-continued

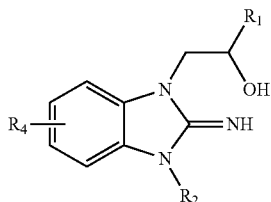

| Compound no./salt | R1 | R2 | R4 |
|---|---|---|---|
| 5 / hydrochloride | phenyl | benzyl | H |
| 6 / hydrochloride | 2-thiophenyl | benzyl | H |
| 7 / hydrochloride | 4-chlorophenyl | benzyl | H |
| 8 / hydrochloride | phenoxymethyl | n-butyl | H |
| 9 / hydrochloride | 3,4-dichlorophenyl | ethyl | H |
| 10 / hydrochloride | 4-chlorophenoxy-n-butyl | n-butyl | H |
| 11 / hydrochloride | 3,4-dichlorophenyl | 4-methylbenzyl | H |
| 12 / hydrochloride | phenoxymethyl | 4-t-butylbenzyl | H |
| 13 / hydrochloride | 3,4-dichlorophenyl | methyl | H |
| 14 / hydrochloride | phenoxymethyl | 4-chlorobenzyl | H |
| 15 / hydrochloride | 4-chlorophenoxy-4-chlorobenzyl | 4-chlorobenzyl | H |
| 16 / hydrochloride | 2-thienyl | 2-(1-morpholino)-ethyl | H |
| 17 / hydrochloride | 2-thienyl | ethyl | H |
| 18 / hydrochloride | phenyl | n-butyl | H |
| 19 / hydrochloride | phenoxymethyl | ethyl | H |
| 20 / hydrochloride | phenoxymethyl | n-propyl | H |
| 21 / hydrochloride | p-chlorophenoxy-methyl | ethyl | H |
| 22 / hydrochloride | phenoxymethyl | (1-piperido)ethyl | H |
| 23 / hydrochloride | 1-adamantyl | methyl | H |
| 24 / hydrochloride | methyl | benzyl | H |
| 25 / hydrochloride | 2-furyl | 2-(1-morpholino)-ethyl | H |
| 26 / hydrochloride | t-butyl | benzyl | H |
| 27 / hydrochloride | 4-methoxyphenyl | methyl | H |
| 28 / hydrochloride | 4-methylphenyl | 2-(N,N-diethyl-amino)ethyl | H |
| 29 / hydrochloride | 4-chlorophenoxy-methyl | n-propyl | H |
| 30 / hydrochloride | phenyl | 2-(1-piperido)ethyl | H |
| 31 / hydrochloride | 4-dimethoxyphenyl | 2-(N,N-diethyl-amino)ethyl | H |
| 32 / hydrochloride | 1-naphthyl | 2-(1-piperido)ethyl | H |
| 33 / hydrochloride | phenoxymethyl | 2-(1-morpholino)ethyl | H |
| 34 / hydrochloride | 2-thienyl | Methyl | H |
| 35 / hydrochloride | 4-chlorophenoxy-methyl | 2-(1-morpholino)ethyl | H |
| 36 / hydrochloride | t-butyl | allyl | H |
| 37 / hydrochloride | 4-ethoxyphenyl | 2-(1-piperido)ethyl | H |
| 38 / hydrochloride | 2-thienyl | 2-(1-piperido)ethyl | H |
| 39 / hydrochloride | 4-bromophenyl | allyl | H |
| 40 / hydrochloride | 4-chlorophenoxy-methyl | 2-(1-piperido)ethyl | H |
| 41 / hydrochloride | phenoxymethyl | allyl | H |
| 42 / hydrochloride | 4-chlorophenoxy-n-propyl | 2-(N,N-diethyl-amino)ethyl | H |
| 43 / hydrochloride | phenyl | n-propyl | H |
| 44 / hydrochloride | phenoxymethyl | methyl | H |
| 45 / hydrochloride | 4-methoxyphenyl | 2-(1-piperido)ethyl | H |
| 46 / hydrochloride | 4-chlorophenoxy-methyl | allyl | H |
| 47 / hydrochloride | 4-methoxyphenyl | benzyl | H |
| 48 / hydrochloride | 4-chlorophenyl | n-propyl | H |
| 49 / hydrochloride | 4-ethoxyphenyl | allyl | H |
| 50 / hydrochloride | 4-methylphenyl | allyl | H |
| 51 / hydrochloride | 3,4-dichlorophenyl | 2-(N,N-diethyl-amino)ethyl | H |
| 52 / hydrochloride | 4-chlorophenoxy-methyl | 4-methylbenzyl | H |
| 53 / hydrochloride | 4-chlorophenyl | n-butyl | H |
| 54 / hydrochloride | 4-chlorophenyl | methyl | H |
| 55 / hydrochloride | phenoxymethyl | 2-(N,N-diethyl-amino)ethyl | H |
| 56 / hydrochloride | 4-chlorophenoxy-methyl | 2-(N,N-diethyl-methyl-aminoethyl) | H |
| 57 / hydrochloride | 4-chlorophenoxy-methyl | methyl | H |
| 58 / hydrochloride | 1-naphthyl | methyl | H |
| 59 / hydrochloride | t-butyl | 4-chlorobenzyl | H |
| 60 / hydrochloride | 4-methylphenyl | n-propyl | H |

TABLE 1-continued

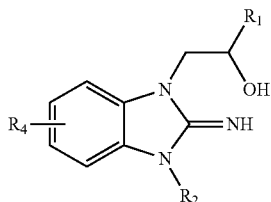

| Compound no./salt | R1 | R2 | R4 |
|---|---|---|---|
| 61 / hydrochloride | methyl | n-propyl | H |
| 62 / hydrochloride | 4-bromophenyl | n-butyl | H |
| 63 / hydrochloride | 4-bromophenyl | benzyl | H |
| 64 / hydrochloride | p-chlorophenyl | allyl | H |
| 65 / hydrochloride | phenyl | methyl | H |
| 66 / hydrochloride | methyl | methyl | H |
| 67 / hydrochloride | 2-furyl | benzyl | H |
| 68 / hydrochloride | 2-furyl | 4-chlorobenzyl | H |
| 69 / hydrochloride | t-butyl | 2-(1-piperido)ethyl | H |
| 70 / hydrochloride | phenoxymethyl | 4-fluorobenzyl | H |
| 71 / hydrochloride | —CH$_2$OCH$_2$C$_6$H$_5$ (benzyloxymethyl) | benzyl | H |
| 72 / hydrochloride | phenoxymethyl | n-octyl | H |
| 73 / hydrochloride | phenoxymethyl | Methylene-1-naphthyl | H |
| 74 / hydrochloride | phenoxymethyl | n-undecyl | H |
| 75 / hydrochloride | phenoxymethyl | benzyl | —CO$_2$C$_2$H$_5$ |
| 76 / hydrochloride | phenoxymethyl | 2-(N,N-dibenzyl-amino)ethyl | H |
| 77 / hydrochloride | benzyl | benzyl | H |
| 78 / hydrochloride | phenoxymethyl | 4-methoxybenzyl | H |

Process: In general, the subject compounds may be prepared by a stepwise alkylation of 2-aminobenzimidazole or a ring-substituted 2-aminobenzimidazole where $R_4$ is other than hydrogen.

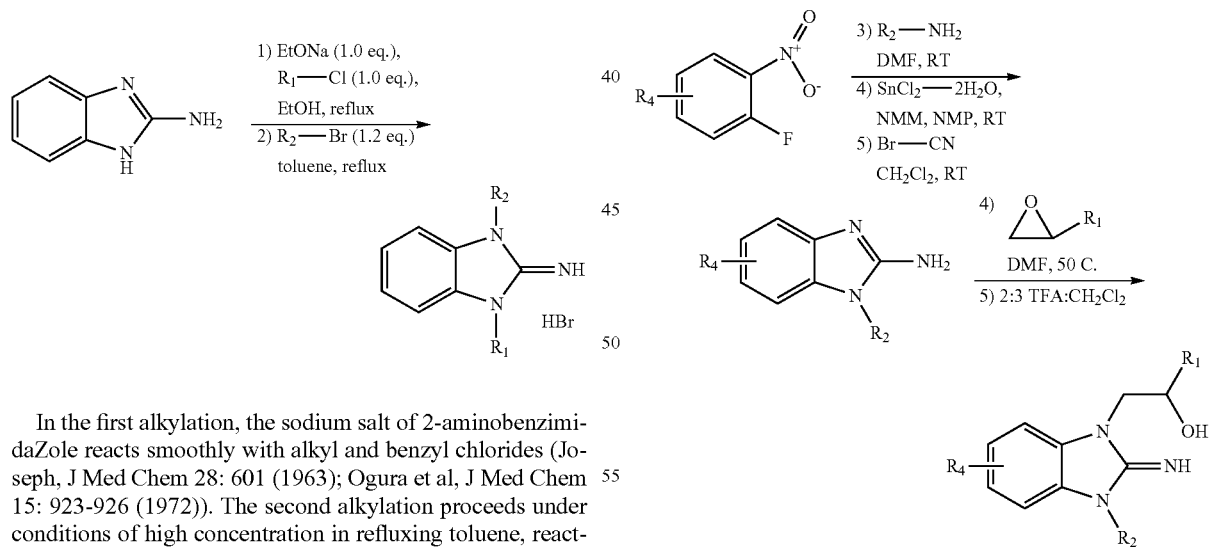

In the first alkylation, the sodium salt of 2-aminobenzimidaZole reacts smoothly with alkyl and benzyl chlorides (Joseph, J Med Chem 28: 601 (1963); Ogura et al, J Med Chem 15: 923-926 (1972)). The second alkylation proceeds under conditions of high concentration in refluxing toluene, reacting exclusively at the 3-position of the imidazole moiety (Rehse, et al., Arch Pharm (Weinheim) 328: 77-80, 1995). The precipitation of the product as the hydrobromide salt prohibits additional alkylation and simplifies the purification.

Alternatively, as described below with respect to the preparation of a combinatorial library, the compounds can be prepared by a process in which a resin-bound 4-fluoro-3-nitroarene is reacted with an amine having the formula R2-NH2, reduced with tin (II) chloride (Bellamy, et al., Tetrahedron Lett 25: 839-842, 1984), cyclized with cyanogen bromide (U.S. Pat. No. 4,002,623), and reacted with a monosubstituted epoxide:

If $R_4$ is a group having the formula CONR$_{16}$R$_{17}$ that group is first introduced by amide coupling with the fluoronitrobenzoic acid.

The subject compounds are incorporated into pharmaceutical compositions or formulations. The compositions will contain pharmaceutically acceptable diluents and/or carriers, i.e. diluents or carriers that are physiologically compatible and substantially free from pathogenic impurities. Suitable excipients or carriers and methods for preparing administrable compositions are known or apparent to those skilled in the art and are described in more detail in such publications as Remington's Pharmaceutical Science, Mack Publishing Co, N.J. (1991). The compositions may also be in the form of controlled release or sustained release compositions as known in the art. For many applications the subject compounds are administered for morning/daytime dosing, with off period at night.

The subject compounds may be used per se, or in the form of their pharmaceutically acceptable salts, such as hydrochlorides, hydrobromides, acetates, sulfates, citrates, carbonates, trifluoroacetates and the like. When compounds contain relatively acidic functionalities, salts can be obtained by addition of the desired base, either neat or in a suitable inert solvent. Examples of pharmaceutically acceptable base addition salts include sodium, potassium, calcium, ammonium, organic amino, or magnesium salts, or the like. When compounds contain relatively basic functionalities, salts can be obtained by addition of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al, "Pharmaceutical Salts", Journal of Pharmaceutical Science, 1977, 66, 1-19).

The neutral forms of the compounds may be regenerated by contacting the salt with a base or acid, and isolating the parent compound in the conventional manner. The parent form of the compound differs from the various salt forms in certain physical properties, such as solubility in polar solvents, but otherwise the salts are equivalent to the parent form of the compound for the purposes of this invention.

In addition to salt forms, this invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity.

Certain compounds of the invention can exist in unsolvated forms as well as solvated forms, including hydrated forms. In general, the solvated forms are equivalent to unsolvated forms and are intended to be encompassed within the scope of the present invention. Certain compounds of the invention may exist in multiple crystalline or amorphous forms. In general, all physical forms are equivalent for the uses contemplated by the present invention and are intended to be within the scope of the invention.

Some of the subject compounds possess asymmetric carbon atoms (optical centers) or double bonds; the racemates, diastereomers, geometric isomers and individual isomers are all intended to be encompassed within the scope of the present invention.

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the invention.

The compounds are generally administered in a "therapeutically effective amount", i.e. the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The contacting is generally effected by administering to the subject an effective amount of one or more compounds having the general formula I (supra), including the various embodiments described above. Generally administration is adjusted to achieve a therapeutic dosage of about 0.1 to 50, preferably 0.5 to 10, more preferably 1 to 10 mg/kg, though optimal dosages are compound specific, and generally empirically determined for each compound.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, lozenges or the like in the case of solid compositions. In such compositions, the mimetic is usually a minor component (from about 0.1 to about 50% by weight or preferably from about 1 to about 40% by weight) with the remainder being various vehicles or carriers and processing aids helpful for forming the desired dosing form. Unit dosage formulations are preferably about of 5, 10, 25, 50, 100, 250, 500, or 1,000 mg per unit. In a particular embodiment, unit dosage forms are packaged in a multipack adapted for sequential use, such as blisterpack comprising sheets of at least 6, 9 or 12 unit dosage forms.

The subject compositions may also be coformulated and/or coadministered with a different compound which also promotes wakefulness, anti-obesity, and/or recovery from general anesthesia or jet lag. Example of co-formulatable drugs include diet pills such as Orlistat (Xenical); narcolepsy drugs such as methylphenidate, racemic amphetamine, dextroamphetamine, and methamphetamine, or modafinil; stimulants such as caffeine; etc.

EXAMPLES

The following examples are provided by way of illustration only and not by way of limitation. Those skilled in the art will readily recognize a variety of noncritical parameters that could be changed or modified to yield essentially similar results.

Example 1

Synthesis of 1-benzyl-2-imino-3-(2-hydroxy-3-phenoxpropyl)benzimidazole hydrobromide (1) (Compound #3)

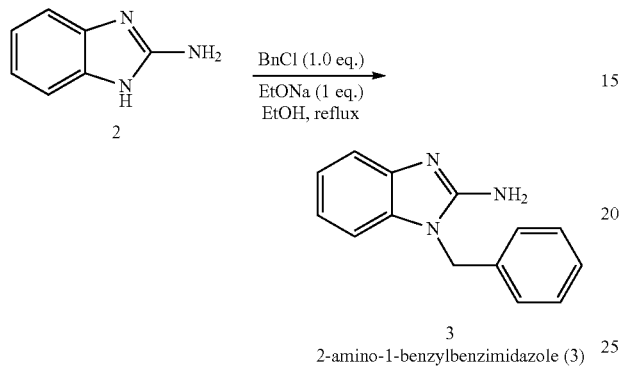

To a solution of 2-aminobenzimidazole (2) (Aldrich, 6 g., 45 mmol) in EtOH (10 mL) is added EtONa (21% in EtOH, 16.83 mL, 45 mmol) and benzyl chloride (5.70 mL, 50 mmol) and the brown solution is refluxed for 3 days under $N_2$ gas.

After cooling to room temperature, the reaction mixture is filtered through celite and concentrated in vacuo. The resulting brown solid is filtered hot in 300 mL acetone and crystallized from approximately 100 mL of acetone, and gives 3 as brown crystals (3.91 g., 39%). Recrystallization of the mother liquor affords additional 3 as brown crystals (0.70 g., 7%). $^1$H-NMR (DMSO-$d_6$) δ5.27 (s, 2H), 6.61 (s, 2H), 6.82 (t, J=8.8 Hz, 1H), 6.93 (t, J=6.4 Hz, 1H), 7.05 (d, J=8.0 Hz, 1H), 7.15 (d, 7.2 Hz, 1H), 7.20 (d, 6.8 Hz, 2H), 7.24 (d, 7.6 Hz, 1H), 7.31 (t, 7.6 Hz, 2H); $^{13}$C-NMR (DMSO-$d_6$) 45.11, 108.30, 115.19, 118.49, 120.88, 127.39, 127.66, 128.91, 134.60, 137.64, 143.34, 155.46.

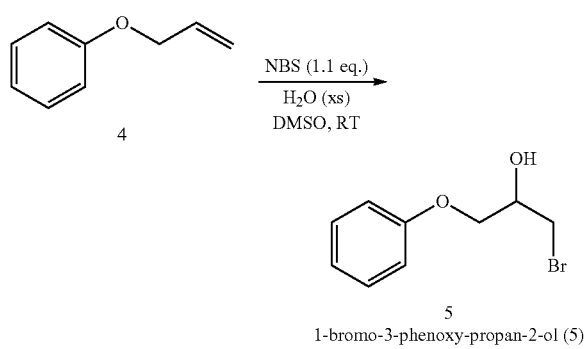

To a room temperature water cooled solution of allyl phenyl ether (4) (Aldrich, 1.00 g., 7.45 mmol) in 5 mL DMSO:$H_2O$ (4:1) is added NBS (1.45 g., 8.15 mmol) as a solid. After 5-10 minutes, the reaction is added to a separation funnel with 100 mL $Et_2O$ and washed three times with 100 mL water, then 100 mL brine solution. The ether layer is dried over $MgSO_4$ and concentrated in vacuo to yield a pale yellow oil (1.59 g., 92%), which is used as is without further purification.

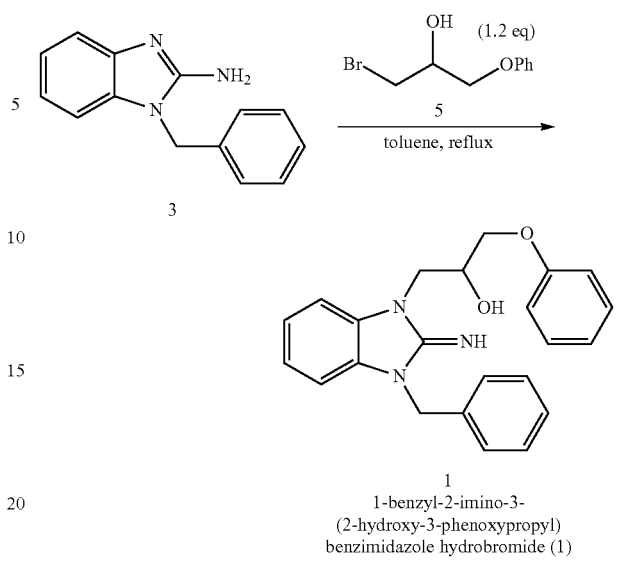

To a solution of 1-bromo-3-phenoxy-propan-2-ol (5) (248 mg, 1.07 mmol) in toluene (2 mL) is added 2-amino-1-benzylbenzimidazole (3) (200 mg, 0.90 mmol) and the mixture is heated at reflux overnight under $N_2$ gas. The reaction mixture is cooled to room temperature and filtered. Crystallization of the collected solid from isopropanol gives 1 as white crystals (85 mg, 23%). Recrystallization of the mother liquor affords additional 1 as white crystals (70 mg., 19%). $^1$H-NMR (DMSO-$d_6$) δ4.12 (s, 2H), 4.33 (s, 1H), 4.43 (s, 2H), 5.57 (s, 2H), 6.96 (m, 3H), 7.21-7.38 (m, 10H), 7.46 (d, J=8.0 Hz, 1H), 7.62 (d, J=7.6 Hz, 1H), 9.18 (s, 2H); $^{13}$C-NMR (DMSO-$d_6$) δ45.58, 46.10, 66.54, 69.43, 110.53, 111.11, 120.71, 123.39, 123.47, 127.11, 127.91, 128.72, 129.39, 129.45, 130.39, 134.56, 150.27, 157.67, 158.33.

Example 2

Preparation of Library of Compounds Using a Combinatorial Method

A library of compounds in which $R_4$ was various groups having the formula CONHR is prepared by the process described above using 4-fluoro-3-nitrobenzoic acid, as follows:

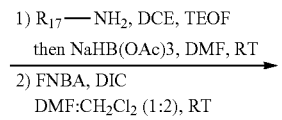

1) $R_{17}$—$NH_2$, DCE, TEOF
then $NaHB(OAc)_3$, DMF, RT
2) FNBA, DIC
DMF:$CH_2Cl_2$ (1:2), RT

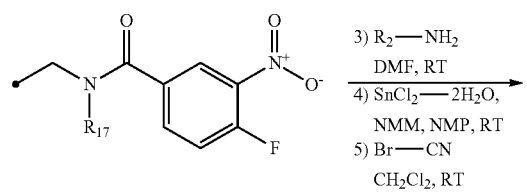

3) $R_2$—$NH_2$
DMF, RT
4) $SnCl_2$—$2H_2O$,
NMM, NMP, RT
5) Br—CN
$CH_2Cl_2$, RT

-continued

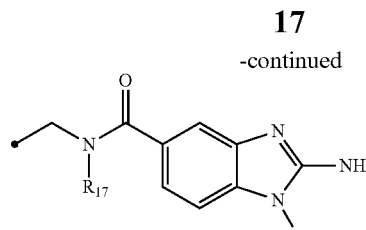

Aldehyde resin is mixed with a primary amine ($R_{17}$—$NH_2$) in dichloroethane (DCE), triethylorthoformate (TEOF), and DMF (containing 1% acetic acid) in a 1:1:1 ratio. After shaken overnight, sodium triacetoxyborohydride (20 eq.) dissolved in DMF is added (Abdel-Magid, et al., Tetrahedron Lett, 3 1: 5595-5598, 1990). After the mixture is shaken at room temperature overnight, the resin is filtered and washed with DMF (3×5 mL), MeOH (3×5 mL), DMF (3×5 mL), MeOH (3×5 mL), and $CH_2Cl_2$ (3×5 mL). The resin was washed twice with 5 mL DMF containing 1% Hunig's base. To the filtered resin is added a mixture of 4-fluoro-3-nitrobenzoic acid (FNBA, 10 eq.) and diisopropylcarbodiimide (DIC, 5 eq.) in 2:1 DMF:DCM. After shaking at room temperature overnight, the resin is filtered and washed with DMF (3×5 mL) and $CH_2Cl_2$ (3×5 mL).

The resin is shaken with a primary amine ($R_2$—$NH_2$) in DMF for 8 hrs, filtered, and washed with DMF (6×5 mL), MeOH (3×5 mL), and $CH_2Cl_2$ (3×5 mL). The aryl nitro group is reduced by the addition of tin (II) chloride dihydrate (20 eq, >2 M) and N-methyl morpholine (NMM, 20 eq.) in N-methyl pyrrolidinone (NMP). After shaken at room temperature overnight, the resin is filtered and washed with NMP (3×5 mL), MeOH (3×5 mL), and $CH_2Cl_2$ (3×5 mL). The resulting resin is shaken at room temperature with cyanogen bromide (5 eq.) overnight, filtered, and washed with $CH_2Cl_2$ (3×5 mL), MeOH (3×5 mL), and $CH_2Cl_2$ (3×5 mL). To produce a free amine, the resin is shaken for 30 min. in $CH_2Cl_2$ with the addition of sodium methoxide in methanol, filtered, and washed with $CH_2Cl_2$ (4×5 mL).

In the final diversification step, the resin is heated at 500 C in DMF with a mono-substituted epoxide [RICH (—$CH_2O$—)]. After shaking for 2 to 4 days the resin is filtered and washed with DMF (5×5 mL), MeOH (3×5 mL), and $CH_2Cl_2$ (3×5 mL). The resin-bound benzimidazole is cleaved from the solid-support by treatment with TFA:$CH_2Cl_2$ (2:3) for 1 hour at room temperature. The library contains a total of 10,560 compounds, prepared using 32 species of group $R_{17}$, 33 of group $R_2$ and 10 of group $R_1$. The library of compounds is depicted in Table 2:

TABLE 2

| # | Structure | R Group | Common Name |
|---|-----------|---------|-------------|
| 1 | —$CH_3$ | 17 | methyl |
| 2 | —$CH_2$—$CH_3$ | 17 | ethyl |
| 3 | —$CH_2CH_2$—$CH_3$ | 17 | propyl |
| 4 | pyrazole-X | 17 | 3-pyrazolyl |
| 5 | cyclopentyl-X | 17 | cyclopentyl |
| 6 | —Ph | 17 | phenyl |
| 7 | pyrimidine-X | 17 | 2-pyrimidinyl |
| 8 | furan-$CH_2$X | 17 | furfuryl |
| 9 | tetrahydrofuran-$CH_2$X | 17 | tetrahydrofurfuryl |
| 10 | 3-keto-isoxazoline-X | 17 | 3-keto-4,5-dihydroisoxazolyl |
| 11 | —$CH_2CH_2OCH_2CH_2CH_3$ | 17 | propoxyethyl |
| 12 | —Bn | 17 | benzyl |
| 13 | pyridine-$CH_2$X | 17 | picolyl |
| 14 | thiophene-$CH_2$X | 17 | 2-thienylmethyl |
| 15 | —$CH_2CH_2N(CH_2)_4$ | 17 | N-ethyl-pyrrolidine |
| 16 | —$CH_2CH_2COOCH_2CH_3$ | 17 | propoxylate ethyl ester |
| 17 | —Bn-4-Me | 17 | 4-methylbenzyl |
| 18 | N-methylpyrrolidinyl-ethyl-X | 17 | 2-(1-methyl-pyrrolidinyl)ethyl |

TABLE 2-continued

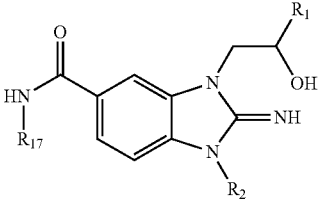

| # | Structure | R Group | Common Name |
|---|---|---|---|
| 19 | 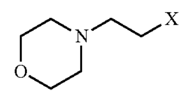 | 17 | 2-(1-morpholino)ethyl |
| 20 | —Bn-3-OMe | 17 | 3-methoxybenzyl |
| 21 | —Bn-3-Cl | 17 | 3-chlorobenzyl |
| 22 | 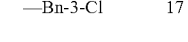 | 17 | 3-(1-pyrrolidinyl-2-one)propyl |
| 23 | —Bn-4-NMe₂— | 17 | 4-(dimethylamino)benzyl |
| 24 | 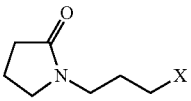 | 17 | piperonyl |
| 25 | —Bn-4-NO₂— | 17 | 4-nitrobenzyl |
| 26 | 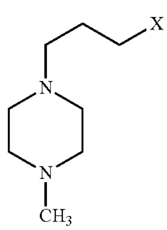 | 17 | 3-(4-methyl-1-piperazinyl)propyl |
| 27 | 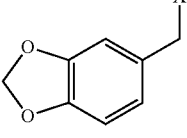 | 17 | 2-methyl-4-quinolinyl |
| 28 | —Bn-3-CF₃ | 17 | 3-trifluoromethylbenzyl |
| 29 | —Bn-2,6-Cl | 17 | 2,6-dichlorobenzyl |
| 30 | —Bn-4-SO₂Me | 17 | 4-(methylsulfonyl)-benzyl |
| 31 | —Bn-3,4,5-OMe | 17 | 3,4,5-trimethoxy-benzyl |
| 32 | —CH₂CH₂CHPh₂ | 17 | 3,3-diphenylpropyl |
| 1 | —CH(CH₃)₂ | 2 | isopropyl |
| 2 | —CH₂CH₂OH | 2 | 2-hydroxyethyl |
| 3 | 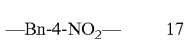 | 2 | 3-pyraxolyl |
| 4 | —CH₂CH₂CH(CH₃)₂ | 2 | isopentyl |
| 5 | —Ph | 2 | phenyl |

TABLE 2-continued

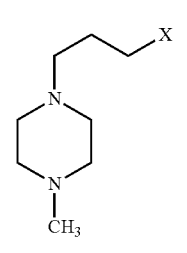

| # | Structure | R Group | Common Name |
|---|---|---|---|
| 6 | 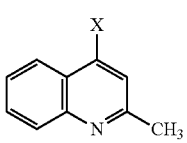 | 2 | 3-pyridyl |
| 7 | 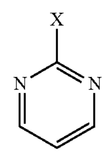 | 2 | 2-pyrimidinyl |
| 8 | 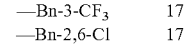 | 2 | furfuryl |
| 9 | 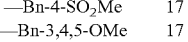 | 2 | cyclohexyl |
| 10 | 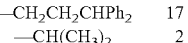 | 2 | N-piperidinyl |
| 11 | 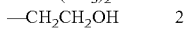 | 2 | tetrahydrofurfuryl |
| 12 | —CH₂CH₂OCH₂CH₂CH₃ | 2 | propoxyethyl |
| 13 | —Bn | 2 | benzyl |
| 14 | 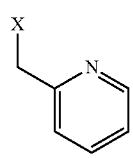 | 2 | 2-picolyl |
| 15 | 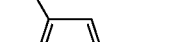 | 2 | 2-thienylmethyl |
| 16 | —CH₂CH₂N(CH₂)₄ | 2 | 2-(1-pyrrolidinyl)ethyl |
| 17 | —CH₂CH₂COOCH₂CH₃ | 2 | propoxylate ethyl ester |
| 18 | —Bn-4-Me | 2 | 4-methylbenzyl |
| 19 | 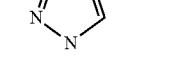 | 2 | 3-quinuclidinyl |

TABLE 2-continued

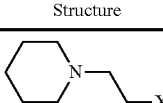

| # | Structure | R Group | Common Name |
|---|---|---|---|
| 20 | 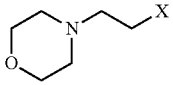 | 2 | 2-(1-piperidino)ethyl |
| 21 | 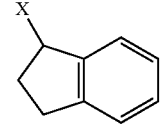 | 2 | 2-(1-morpholino)ethyl |
| 22 | 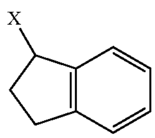 | 2 | 1-idanyl |
| 23 | —Bn-3-OMe | 2 | 3-methoxybenzyl |
| 24 | —Bn-3-Cl | 2 | 3-chlorobenzyl |
| 25 | 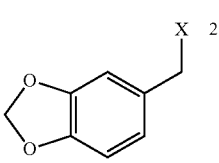 | 2 | 3-(1-morpholino)propyl |
| 26 | —Bn-4-NMe$_2$ | 2 | 4-(dimethylamino)benzyl |
| 27 | 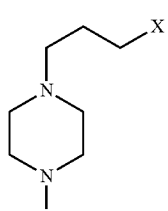 | 2 | piperonyl |
| 28 | —BN-4-NO$_2$ | 2 | 4-nitrobenzyl |
| 29 | 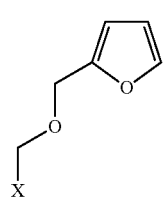 | 2 | 3-(4-methyl-1-piperazinyl)propyl |
| 30 | —Bn-3-CF$_3$ | 2 | 3-trifluoromethylbenzyl |
| 31 | —Bn-2,4-Cl | 2 | 2,4-dichlorobenzyl |
| 32 | —Bn-4-SO$_2$Me | 2 | 4-(methylsulfonyl)benzyl |
| 33 | —Bn-3,4,5-OMe | 2 | 3,4,5-trimethoxybenzyl |
| 1 | —CH$_2$OPh | 1 | phenoxymethyl |
| 2 | —CH$_2$OCH(CH$_3$)$_2$ | 1 | isopropoxymethyl |
| 3 | —CH$_2$OPh-4-OMe | 1 | 4-methoxy-phenoxymethyl |
| 4 | —CH$_2$OPh-4-C(CH$_3$)$_2$ | 1 | 4-t-butyl-phenoxymethyl |
| 5 | 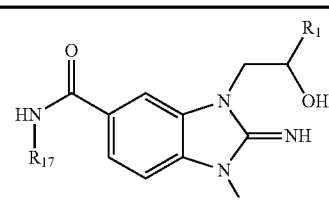 | 1 | 2-furfuryloxymethyl |

TABLE 2-continued

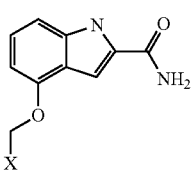

| # | Structure | R Group | Common Name |
|---|---|---|---|
| 6 | —CH$_2$OPh-2-Me | 1 | 2-methyphenoxymethyl |
| 7 | —CH$_2$OPh-4-Cl | 1 | 4-chlorophenoxymethyl |
| 8 | —Ph | 1 | phenyl |
| 9 | (structure) | 1 | 2-carbamyl-5-inolyl-oxymethyl |
| 10 | —CH$_2$OPh-4-NO$_2$ | 1 | 4-nitrophenoxymethyl |

Example 3

Cell-Based Transcription Assay for OX2R Agonists

DNA Construction: Open reading frames of OX1R, OX2R and GRP (control) receptor were inserted into a bicistronic retrovirus expression vector, pMXs-IRES-puror (pMXs-IP), which carried a FLAG™ epitope cDNA sequence at the beginning of the ORF sequences encoding their human polypeptides.

Transfection and retrovirus production: Transfection was carried out using FuGENE 6 (Roche Diagnostics Corp.) according to the manufacturer's recommendations. Retroviruse fluid was harvested after 48 hours post transfection.

Cell lines: To generate receptor expressing cells, CHO cells harboring ecotropic retroviral receptor were infected with a retroviral supernatant. After 24 hours post infection, the retrovirus supernatant was removed and infected cells were selected with 10 µg/ml of puromycin (Sigma-Aldrich, St. Louis, Mo.).

To generate stable indicator cell lines, constitutively receptor expressing CHO cell lines were transfected with NFAT-responsive luciferase reporter plasmid (pNFAT-TA-Luc) together with pSV2neo which carried antibiotic resistance gene, by using FuGENE6 (Roche Diagnostics, Roskilde, Denmark). After 24 hours, the transfected cells were selected with 1 mg/ml G418 (invitrogen). G418 resistance cells were seeded and isolated single clones.

Luciferase reporter assay: The indicator cells were seeded at 5,000/well in a 384-well plate and incubated at 37° C. for overnight. 2.5 µl of library compound was added in each wells and incubated at 37° C. for 7-8 hours. After removed media, cells were lysed and determined the luciferase activity with Bright-Glo™ (Promega, Madison, Wis.).

Intracellular Calcium Transient Assay: The CHO cell lines expressing appropriate G-protein coupled receptors were incubated with 2 µM Fura-2 AM (Invitrogen, Carlsbad, Calif.) in a loading buffer (Hank's balanced salt solution containing 25 mM HEPES, 2.5 mM probenecid and 0.1% bovine serum albumin) at room temparature for 1 hour. The cells were harvested by centrifugation and washed the cell pellet with the loading buffer three times, then suspended in the loading buffer at 2×10⁶ cells/ml.

0.5 ml aliquot of the cell suspension was stimulated by addition of 5 μl of compound dissolved in DMSO. Changes of [$Ca^{2+}$]i transients in cells were measured at RT by using CAF-110 Intracellular Ion Analyser (JASCO, Tokyo) with the excitation wave lengths of 340 nm and 380 nm and emission wavelength of 500 nm Example 4

Identification and Characterization of Cyclic Guanidinyl Compound No. 130699

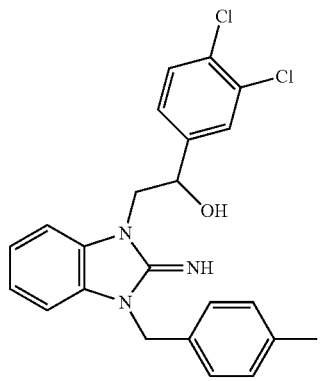 [SMILES: Cc1ccc(Cn2c(=N)n(CC(O)c3ccc(Cl)c(Cl)c3)c3ccccc32)cc1]

Compound 130699 (also referred to as #6037874 and Yan 7874) induces robust Ca2+ response in OX2R-expressing CHO cells, a weaker response in OX1R-expressing cells, and no response in cells expressing an unrelated Gq-coupled GPCR (GRP receptor). This compound also induces dramatic activation in transcriptional reporter assays in HEK293T cells transiently co-transfected with the NFAT-luciferase reporter plasmid and a receptor cDNA plasmid. We also confirmed reporter activation in a distinct CRE reporter system:

| | Assay | | | |
|---|---|---|---|---|
| | OX2R_NFTA (1) | OC2R_NFTA (2) | OX2R_CRE | No Receptor_CRE |
| Fold Induction | 10.94 | 35.566 | 5.1935 | 0.797 |

Metabolism: 2 μM Yan7874 was incubated in 1 ml 0.1 M Tris/0.5% $NaHCO_3$/3 mm $MgCl_2$ solution with 1 mg mouse CD-1 S9 protein (In Vitro Technologies, Baltimore, Md.) at 37° C. Cofactors necessary for phase I and II metabolism were added as recommended by In Vitro Technologies (phase I: 1.7 mg/ml NADP, 7.8 mg/ml glucose-6-phophate, 6 U/ml glucose-6-phosphate dehydrogenase; phase II additionally add 1.9 mg/ml uridine 5'-diphospho-α-D-glucuronic acid and 100 μg/ml 3'-phosphoadenosine-5'-phophosulphate). Protein was precipitated by the addition of 1 volume of methanol. Samples in 50:50 buffer:methanol+0.1% added formic acid were analyzed as follows. An analytical method was developed to detect Yan7874 using LC/MS/MS. Yan7874 was detected in SIM mode using the 426.0 to 105.0 transition (426.0 protonated parent ion/105.0 daughter ion) and had a retention time of 6.35 minutes when run on a 12 minute water/methanol (+0.1% formic acid) gradient (0 to 100% methanol) using a Phenomenex synergi fusion RP column (5 micron packing, 75×2 mm size). The fraction of parent compound remaining was plotted over time and a curve fit to the data. The time at which 50% of compound remains is designated the in vitro half-life. See FIG. 1 showing that compound 130699 (referred to as Yan7874 here) is relatively stable in vitro using hepatocyte S9 fractions.

Pharmacokinetics: Methods: Chembridge Compound 6037874 ("Yan7874") was provided as a powdered stock and dissolved in DMSO at 50 mg/ml. The compound was formulated as 5% DMSO/5% Cremaphor EL/90% 5% dextrose, pH 7.2 such that compound could be administered to mice at 10-20 mg/kg in a volume of 0.2 ml by IV bolus.

Twenty one C57BL/6 mice (NCI, male, 6 weeks of age) were weighed and injected with 10 mg/kg compound formulated as described above IV in 0.2 ml. A dose of 20 mg/kg was tried initially, but the first two mice injected at this dose showed a relatively severe reaction marked by a mild seizure and reduced activity for several hours. The dose was lowered to 10 mg/kg and no acute reactions were noted, so the remainder of the experiment was conducted at this dose. The mice were sacrificed in groups of three by inhalation overdose of CO2 and blood and brain obtained. Plasma was subsequently isolated from the plasma by centrifugation in a refrigerated microcentrifuge at 10,000 rpm for 10'. The brain was washed extensively with PBS, blotted dry, weighed, and snap frozen in liquid nitrogen.

A second experiment was conducted using 24 C57BL/6 mice (NCI, male, 6 weeks of age). These mice were weighed and injected with 20 mg/kg of compound formulated as described above IP in 0.2 ml. A dose of 30 mg/kg was tried initially, but one of the two mice injected at this dose appeared to show abdominal guarding and decreased activity for up to one hour. The dose was lowered to 20 mg/kg and no acute reactions were noted, so the remainder of the experiment was conducted at this dose. The mice were sacrificed as above in groups of three by inhalation overdose of CO2 and blood and brain obtained and processed as above.

An analytical method was developed to detect Yan7874 using LC/MS/MS. Yan7874 was detected in SIM mode using the 426.0 to 105.0 transition (426.0 protonated parent ion/105.0 daughter ion) and had a retention time of 6.35 minutes when run on a 12 minute water/methanol (+0.1% formic acid) gradient (0 to 100% methanol) using a Phenomenex synergi fusion RP column (5 micron packing, 75×2 mm size).

A standard curve was developed in plasma in the following manner. 100 μl of plasma is spiked with varying concentrations of Yan7874. The plasma is allowed to sit 10' at room temperature after vortexing. 200 μl of acetonitrile is added to precipitate plasma proteins and release bound drug. After vortexing, the sample is incubated 10' at room temperature. 700 μl of PBS is added and the sample is centrifuged at 14,000 rpm in a standard microcentrifuge for 5'. 900 μl of supernatant is added to 1 ml of PBS. The entire sample is passed over a Waters OASIS HLB solid phased extraction column already primed by addition of 2 ml methanol and 2 ml $H_2O$. The column is washed once with 2 ml of 5% methanol/2% NH4OH in $H_2O$ and once with 2 ml of 5% methanol/2% acetic acid in $H_2O$ and compound is eluted by addition of 2 ml of methanol containing 2% $NH_4OH$. 500 μl of this is added to 500 μl of $H_2O$ containing 0.2% formic acid (final formic acid 0.1%). Samples are prepared in the same manner without addition of spiked compound. Brain tissue is prepared by homogenizing in 3× volume of PBS (weight in grams×3=volume in ml to add). 100 μl of blank brain lysate is used for preparation of standard curve samples while 100 μl of sample brain lysate is used for preparation of samples. To calculate brain levels, the concentration in ng/ml calculated from the standard curve is multiplied by the total volume of lysate (a value in ml estimated from the 3× volume of PBS added +1× volume to account for brain tissue itself) and then divided by the weight of the brain in grams. A value of 3× above the signal obtained from blank plasma or brain lysate is designated the limit of detection (LOD). The LOD for plasma is 2640 and for brain 459. The limit of quantitation (LOQ) is the lowest concentration at which back calculation yields a concentration within 20% of theoretical. The LOQ for both plasma and brain is 5 ng/ml. In general back calculation of points on both curves yielded values within 20% of theoretical over 4 orders of magnitude (10,000 to 5 ng/ml) for both sample types.

Figure 2:
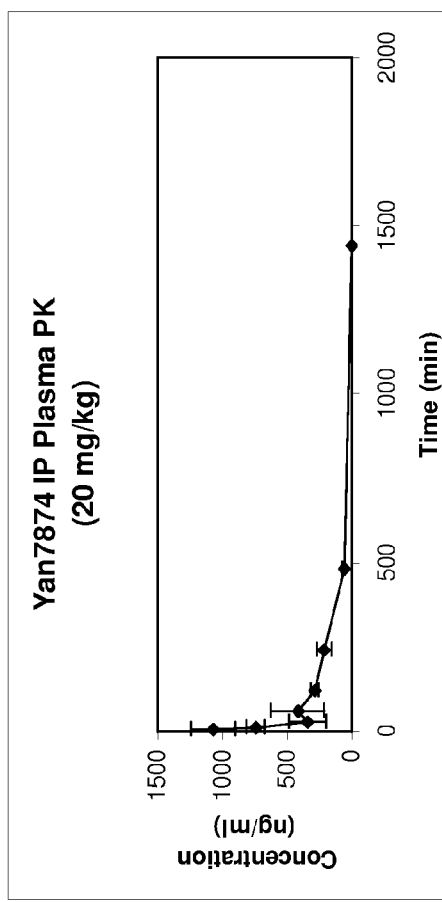
Figure 2:
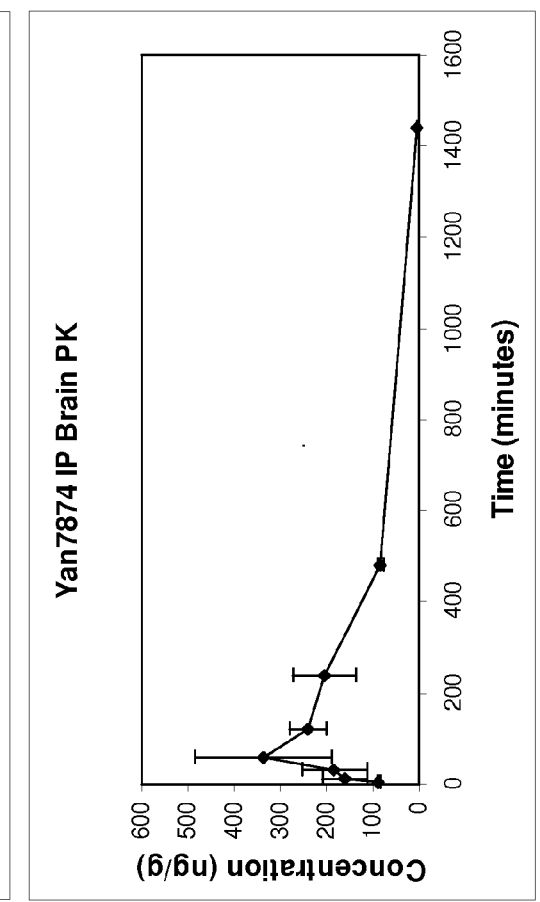
Figure 2:
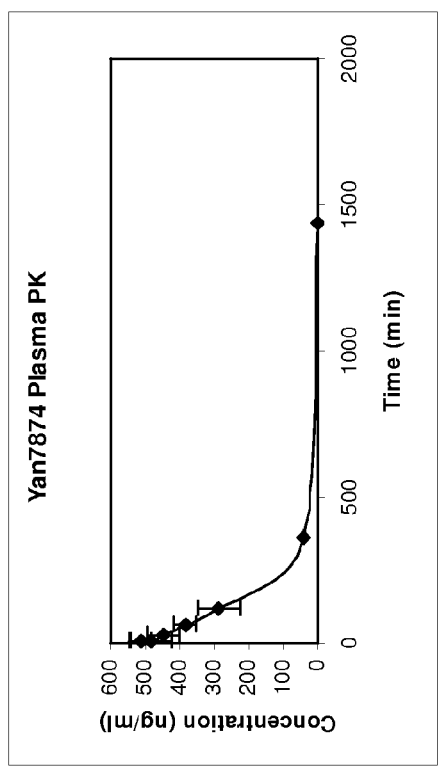
Figure 2:
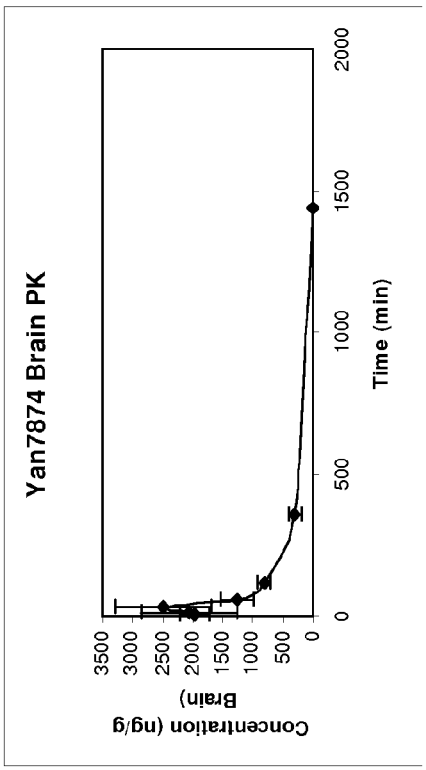

Results: The compound shows good brain penetration, as predicted, with levels of 5 ng/g persisting at 24 hours post-injection and peak levels of ~2.5 µg/g brain tissue achieved 30 minutes after dosing (see FIG. 2). Indeed, its peak brain concentrations (which occur ~30 min later) are ~5 fold higher than the peak levels in plasma. The pharmacokinetic data were modeled for the plasma data using the noncompartmental model of WinNonlin (sparse sampling option), with the following parameters estimated:

| IV Pharmacokinetics (10 mg/kg) | |
|---|---|
| Plasma: | |
| AUC*: | 91803 min*ng/ml |
| Clearance: | 2.1 ml/min |
| Terminal half life: | 91.3 min |
| Cmax: | 512 ng/ml |
| Brain: | |
| AUC | 485,627 min*ng/g |
| Clearance: | 0.4 g/min |
| Terminal half life: | 187.5 min |
| Cmax: | 2481 ng/g |
| Blood Brain Penetration Ratio: | |
| Cmax brain/Cmax plasma: | 4.8 |
| AUC brain/AUC plasma: | 5.2 |
| IP Pharmacokinetics (20 mg/kg) | |
| Plasma: | |
| AUC: | 143,707 min*ng/ml |
| Clearance: | 2.7 ml/min |
| Terminal half life: | 165 min |
| Cmax: | 1076 ng/ml |
| Brain: | |
| AUC | 133,194 min*ng/g |
| Clearance: | 2.9 g/min |
| Terminal half life: | 203.5 min |
| Cmax: | 337 ng/g |
| Blood Brain Penetration Ratio: | |
| Cmax brain/Cmax plasma: | 0.3 |
| AUC brain/AUC plasma: | 0.9 |

*Area under the concentration-time curve

Example 5

SAR Studies Around the Cyclic Guanidinium Scaffold of Compound 130699

The half-life of compound 3a (FIG. 3) for in vitro Phase I and combined Phase I+II metabolism in S9 fractions was 68 and 56 min respectively. Most importantly, compound 3a shows good brain penetration, with levels of 5 ng/g persisting at 24 hours post-injection and peak levels of ~2.5 µg/g brain tissue achieved 30 minutes after dosing (21 mice, dosing: 10 mg/Kg iv). Plasma pharmacokinetic data were excellent: Area under the concentration-time curve (AUC)=91803 min*ng/ml; Clearance=2.1 ml/min; Terminal half-life=91.3 min We initiated a chemistry program around the cyclic guanidinium scaffold using a flexible synthetic route. Based on this practical synthetic route, we have assembled structure-activity relationship (SAR) data. See FIG. 3. The chiral secondary alcohol in compounds 3 (marked with a *) is clearly important as oxidation to a ketone (see compounds 4a-b, 4f, 4h-i) totally abolishes activity. Also, acetylation of this alcohol and the imine nitrogen results in inactive compounds (see structure 5). SAR for the top aromatic ring indicates that bulky ($CMe_3$, compound 3e) or electron-withdrawing ($NO_2$, compound 3d) substitution in the para-position is dendrimental to activity. The relative activity in the series 3f>3b>3c highlights the preference for a para-methoxy substitutent. The ortho-nitro substituted analog 3h is equipotent to the dichloro-substituted lead 3a.

Example 6

Orexin Peptides and Agonists Prevent Cataplexy and Improve Wakefulness

Aspects of this example, including more detailed descriptions of the production of the CAG/orexin-transgenic mice, the cataplexy testing, cannulation (i.c.v.) and orexin administration and EEG/EMG recordings were published in Mieda et al., PNAS USA Mar. 30, 2004; 101(13):4649-54.

We administered orexin-A, a nonselective agonist for orexin receptor type 1 (OX1R) and OX2R. The dose and route of administration chosen (3 nmol per mouse i.c.v.) is comparable to that used previously to examine the effects of orexin-A on behavior and metabolism in rodents, and is effective in dose-response studies of sleep/wakefulness in wild-type mice, but produces no detectable effects in knockout mice lacking both OX1R and OX2R genes.

We examined whether i.c.v. orexin-A administration suppresses cataplectic arrests in orexin/ataxin-3-transgenic mice. By using a randomized crossover design, we administered vehicle and orexin-A to all mice during separate experimental sessions. When narcoleptic mice were treated with vehicle alone, they exhibited variable frequencies of arrests, as well as variable cumulative times spent in arrests during the first 3 h after injections. In contrast, when the same mice were administered orexin-A, the frequency of arrests and overall time spent in cataplexy were significantly reduced in each mouse during the same 3-h time period, despite increases in observable wakeful activity. Thus, i.c.v. administration of orexin-A is sufficient to acutely suppress behavioral arrests in this model of narcolepsy.

To quantify the effects of orexin-A administration on sleep/wake status, we recorded EEG/EMG in orexin/ataxin-3 mice, as well as wild-type controls. Because narcoleptic humans and animals exhibit sleepiness and cataplexy during their respective active phases, orexin-based therapies are preferably administered to humans during the active phase. Nevertheless, some pharmacological effects of exogenous orexins have been reported to vary with time of day (Zeitgeber-dependent effects). We therefore examined the effects of orexin-A administrations in mice both at the onset of the dark (active) phase as well as during the light (resting) phase, again by using a randomized crossover design.

Patterns of wakefulness, non-REM sleep, and REM sleep revealed a robust arousal effect of orexin-A in transgenic narcoleptic as well as wild-type mice. Central administration of 3 nmol of orexin-A strikingly increased wakefulness and suppressed both non-REM and REM sleep, regardless of genotype and time of administration. Interestingly, equivalent doses of orexin-A, administered during either the nocturnal or diurnal phases, produced arousal with greater effectiveness in narcoleptic mice compared with wild-type controls. Whereas both wild-type and narcoleptic mice exhibited similar amounts of wakefulness and non-REM sleep in a 3-h period after vehicle administrations, orexin-A induced significantly greater amounts of wakefulness in orexin/ataxin-3-transgenic mice than it did in wild-type mice. These increases in wakefulness were essentially mirrored by significantly greater suppressions of non-REM sleep in narcoleptic animals.

As expected, orexin/ataxin-3 mice exhibited significantly higher amounts of REM sleep than did wild-type controls during the dark phase under baseline (vehicle-administered) conditions. Critically, orexin-A effectively suppressed this elevation of REM sleep in narcoleptic mice. Again, orexin-A was more effective at suppressing REM sleep in narcoleptic mice than in wild-type controls, regardless of the time of administration.

Unlike effects reported with amphetamine administrations in humans, rats, and mice, no immediate rebounds of sleep were observed after dark-phase or light-phase orexin-A administrations. Narcoleptic animals maintained a statistically significant increase of cumulative wakefulness and a decrease of cumulative sleep, even after 24 h after a nocturnal administration of orexin-A. When orexin-A was administered diurnally, mice of both genotypes recovered sleep losses by the 24-h mark, but this recovery was gradual in nature.

Figure 3:
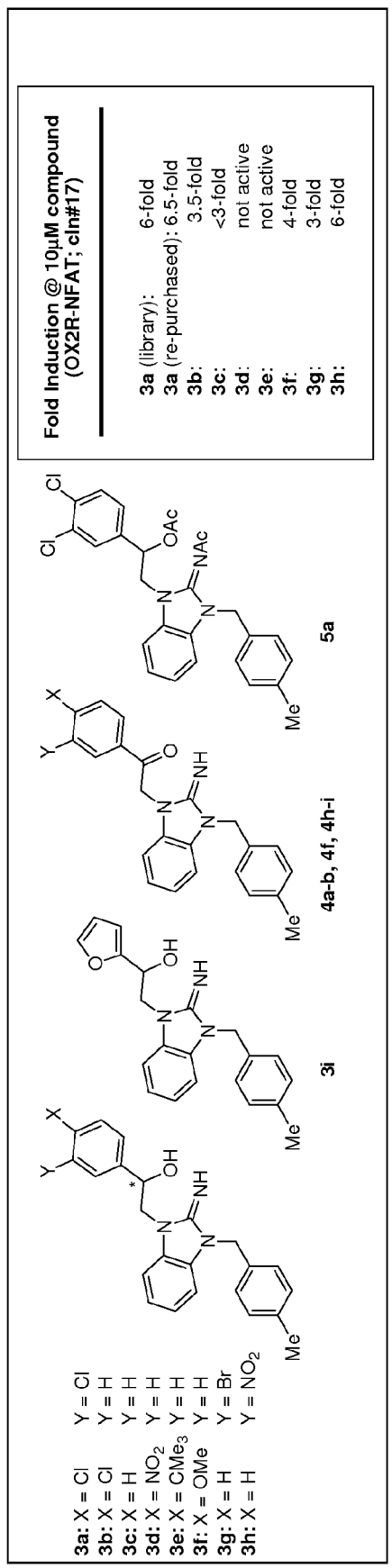

The same protocols demonstrate that orexin agonists (e.g. Tables 1, 2; FIG. 3) similarly prevent cataplexy and improve wakefulness at 10 mg/kg administered either orally in food or water, or i.p. Overall, these results demonstrate the feasibility of treating symptoms of narcolepsy-cataplexy by using pharmacological agonists of orexin receptors.

Example 7

Orexin agonists abbreviate emergence from general anesthesia—aspects of this example were published by Kelz et al. (PNAS, Jan. 29, 2008, vol. 105, no. 4, p. 1309-1314).

Loss and Return of Righting Reflex. Induction and emergence from isoflurane or sevoflurane were defined behaviorally as the respective loss and return of the righting reflex and were evaluated as follows. Wild-type C57BL/6J male mice aged 8-14 weeks (Jackson Laboratories). were placed in cylindrical gas-tight, controlled-environment chambers arrayed in parallel (35). After 90 min of habituation with 100% oxygen each day on two successive days, anesthesia was induced with a Drager model 19.1 isoflurane or sevoflurane vaporizer by using 8-12 stepwise incremental increases in the concentration of anesthetic gas dissolved in 100% oxygen. Anesthetic gas concentrations were determined in triplicate during the last 2 min at each step (35). Initial volatile anesthetic concentrations were 0.44% isoflurane or 0.96% sevoflurane. After 15 min at each concentration to allow for equilibration of the mouse with the anesthetic vapors, the concentration of volatile anesthetic was increased by 6±3% of the preceding value. Peak volatile anesthetic concentrations were 1.19% isoflurane or 1.52% sevoflurane. At the end of each 15-min interval, the cylindrical chambers were rotated 180°. A mouse was considered to have lost the righting reflex if it did not to turn itself prone onto all four limbs within 2 min. After the last mouse lost its righting reflex, volatile anesthetic concentration was increased one additional time before measurements of emergence time, which was defined as the duration that elapsed until each mouse regained its righting reflex by turning prone onto all four feet. Mouse temperature was maintained between 36.6±0.6° C. by submerging the controlled environment chambers in a 37° C. water bath. In an effort to minimize both the number of mice used and the number of anesthetic exposures, induction and emergence from anesthesia in orexin/ataxin-3 mice and sibling controls were performed during the same experiment.

Pharmacologic Inhibition of Orexin Signaling and Righting Reflex Studies. To determine the effect of the orexin-1R antagonist, SB-334867-A (Tocris Bioscience), on induction of anesthesia, 24 C57BL/6J mice were evaluated for both the concentration at which the righting reflex was lost as well as a separate experiment to measure the latency to loss of righting. Thirty minutes before determining isoflurane sensitivity, one-third of the mice received an i.p. injection of vehicle (10% encapsin and 2% DMSO in sterile water), and the other two-thirds received 5 mg/kg or 20 mg/kg of freshly prepared SB-334867-A dissolved in vehicle (21) and administered i.p. at 20 ml/kg. All three groups of mice were exposed to 1.25% isoflurane. Righting reflex was checked every 15 s. To determine the dose-response curve for loss of righting, stepwise increases in isoflurane concentration were performed every 15 min as described above. To eliminate the questions about the duration of action of SB-334867-A, emergence from isoflurane anesthesia in wild-type C57BL/6J mice was studied as described below rather than after the typical 3 h required to generate induction dose-response curves. C57BL/6J mice were anesthetized in controlled-environment chambers (35) with 1.25% isoflurane for 90 min. Individual mice were rapidly removed, injected with an i.p. bolus of either vehicle, 5 mg/kg, or SB-334867-A, 20 mg/kg, doses known to reverse orexin-A-mediated behaviors (21, 22). All i.p. volumes were delivered at 20 ml/kg over 20-30 s Immediately after injection, mice were returned to the controlled-environment chambers where they continued to breathe 1.25% isoflurane for an additional 30 min before anesthetic gases were discontinued and emergence time$_{RR}$ was recorded as described above Results. While orexin-1R antagoinist SB-334867-A produced a dose-dependent delay in emergence of wild type C57BL/6J mice exposed to isoflurane, and significantly delayed emergence at 20 mg/kg i.p. ($F_{2,45}$=8.80, P<0.001), the same protocols demonstrate that orexin agonists (e.g. Tables 1, 2, FIG. 3) produce a dose-dependent abbreviation in emergence of wild type C57BL/6J mice exposed to isoflurane, and significantly abbreviated emergence at 10 mg/kg administered either orally in food or water, or i.p.

Example 8

OX2R selective agonists abbreviate recovery from jet lag. An established animal model may be used to assess the effects of orexin agonists on jet lag. In one suitable protocol, the rhythms in rest/activity and body temperature are studied in male 6-week-old B6D2F1 mice having a radio transmitter (Physio Tel, TA 10 TA-F20; Data Sciences, St. Paul, Minn.) implanted into the peritoneal cavity, which records locomotor activity and body temperature every 10 minutes. The mice are synchronized to standard lighting conditions of LD12:12, with lights on from 6 a.m. to 6 p.m., for 3 weeks and then undergo experimental jet lag produced by an 8-hour advance of light/dark cycle. Control and treatment mice are then monitored for the time taken to recalibrate the animals' rest/activity and temperature rhythms to the new cycle. Use of this protocol demonstrates that orexin agonists (e.g. Tables 1, 2, FIG. 3) abbreviate the time required to reset circadian rhythms shifted by jet lag at 10 mg/kg administered either orally in food or water, or i.p.

Example 9

OX2R Selective Agonists Reduce Diet-Induced Obesity

To examine whether enhanced OX2R signaling causes resistance to diet-induced obesity, an OX2R selective agonist, [Ala11, D-Leu15] Orexin-B (Akanmu and Honma, 2005 Brain. Res. 1048. 138-145.; Asahi et al., 2003 Bioorg. Med. Chem. Lett. 13.

111-113) was continuously infused in the lateral ventricles of wild-type mice for 14 days. The administration of the OX2R selective agonist (0.5 nmol/d) suppressed weight gain on a high fat diet, without altering weight homeostasis on a low fat diet. There was no effect of the OX2R selective agonist for OX2R-deficient mice on a high fat diet (n=4, weight gain 3.33±0.61 g), verifying the selectivity of the agonist in vivo. Following 14 days, the agonist-infused wild-type mice gained significantly less fat mass than did the vehicle-injected mice on a high fat diet, and no effect was observed on a low fat diet. Administration of the OX2R selective agonist reduced food intake only on a high fat but not on low fat diet. After 14 days of OX2R agonist administration, we observed reduced hypothalamic mRNA expression of orexigenic factors, NPY and AGRP on a high fat diet, compared to those on a low fat diet. We detected no significant change in LEPR, or other downstream transcripts POMC, SOCS3, or STAT3. The same experimental protocol demonstrates that orexin agonists (e.g. Tables 1, 2, FIG. 3) similarly inhibit diet-induced obesity at 10 mg/kg administered either orally in food or water, or i.p.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for promoting enhanced wakefulness of a person subject determined to be in need thereof, comprising the step of:
   (a) orally administering to the subject a type-2 orexin receptor (OX2R) agonist of formula I:

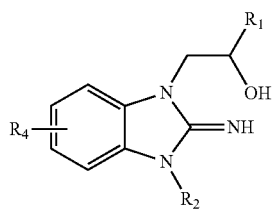

in which:
$R_1$ is
substituted or unsubstituted alkyl;
substituted or unsubstituted cycloalkyl;
substituted or unsubstituted alkenyl;
adamantyl;
substituted or unsubstituted phenyl;
a 5- or 6-membered optionally substituted saturated or unsaturated heterocyclic group having from one to three heteroatoms selected from nitrogen, oxygen and sulfur;
substituted or unsubstituted benzyl;
a saturated or unsaturated fused ring carbocyclic group having from 8 to 10 ring atoms; or
$CH_2XR_5$, where X is oxygen, sulfur, —NH— or —$CH_2$— and $R_5$ is substituted or unsubstituted alkyl; substituted or unsubstituted cycloalkyl; substituted or unsubstituted phenyl; substituted or unsubstituted benzyl; 2-carbamide-indolyl; or a 5 to 9-membered optionally substituted saturated or unsaturated heterocyclic group having from one to three heteroatoms selected from nitrogen, oxygen and sulfur;

$R_2$ is
substituted or unsubstituted alkyl;
substituted or unsubstituted cycloalkyl;
substituted or unsubstituted alkenyl;
substituted or unsubstituted alkoxyalkyl;
a 5- or 6-membered optionally substituted saturated or unsaturated heterocyclic group having from one to three heteroatoms selected from nitrogen, oxygen and sulfur;
—$(CH_2)_nR_3$, where $R_3$ is (i) a 5- to 9-membered optionally substituted saturated or unsaturated heterocyclic group having from one to three heteroatoms selected from nitrogen, oxygen and sulfur; (ii) —$NR_6R_7$ where $R_6$ and $R_7$ are independently selected from hydrogen, methyl, ethyl and benzyl; or (iii) $COOR_8$ where $R_8$ is alkyl; and n is 2 or 3;
substituted or unsubstituted phenyl;
substituted or unsubstituted benzyl;
a saturated or unsaturated fused ring carbocyclic group having from 8 to 10 ring atoms; or
methylene-1-naphthyl; and $R_4$ is
hydrogen;
$(CH_2)_mCOOR_{15}$ where $R_{15}$ is alkyl or substituted alkyl; and m is 0, 1 or 2;
$CONR_{16}R_{17}$, where $R_{16}$ and $R_{17}$ are independently (i) hydrogen; (ii) alkyl or substituted alkyl; (iii) cycloalkyl; (iv) alkoxyalkyl; (v) a 5- to 10-membered optionally substituted saturated or unsaturated heterocyclic group having from one to three heteroatoms selected from nitrogen, oxygen and sulfur; (vi) a saturated or unsaturated fused ring carbocyclic group having from 8 to 10 ring atoms; (vii) substituted or unsubstituted phenyl; (viii) $(CH_2)_pR18$ where $R_{18}$ is a 5- or 6-membered optionally substituted saturated or unsaturated heterocyclic group having from one to three heteroatoms selected from nitrogen, oxygen and sulfur, and p is 1, 2 or 3; (ix) optionally substituted benzyl; or (x) an aralkyl group comprising a chain of from 1 to 4 methylene groups substituted by one or two phenyl groups;
$C_1$-$C_4$ alkoxy;
optionally substituted phenoxy;
$SO_2NR_{19}R_{20}$ where $R_{19}$ and $R_{20}$ are independently hydrogen, optionally substituted alkyl or phenyl;
$NR_{21}R_{22}$, wherein $R_{21}$ and $R_{22}$ are independently hydrogen, alkyl, optionally substituted phenyl or optionally substituted benzyl;
$COR_{23}$ where $R_{23}$ is alkyl or is $NR_{21}R_{22}$;
$COOR_{24}$ where $R_{24}$ is hydrogen, alkyl, or benzyl; or
$SO_2R_{25}$ where $R_{25}$ is alkyl or $NR_{21}R_{22}$;
or a pharmaceutically acceptable salt thereof, or prodrug thereof.

2. The method of claim 1, wherein the agonist is of formula:

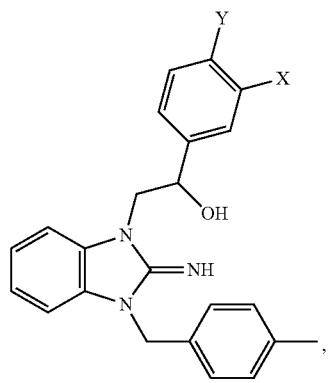

X is Cl and Y is Cl,
X is Cl and Y is H,
X is H and Y is H,
X is OMe and Y is H
X is H and Y is Br, or
X is H and Y is NO$_2$.

3. The method of claim 1 wherein the agonist is of formula:

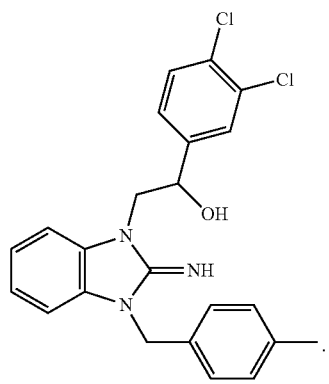

4. The method of claim 1, further comprising detecting a resultant enhanced wakefulness.

5. The method of claim 2, further comprising detecting a resultant enhanced wakefulness.

6. The method of claim 3, further comprising detecting a resultant enhanced wakefulness.

7. The method of claim 1 comprising administering to the subject the OX2R agonist regularly and chronically.

8. The method of claim 1 comprising administering to the subject the OX2R agonist in conjunction with an effective amount of a different compound which promotes wakefulness.

9. The method of claim 2 comprising administering to the subject the OX2R agonist in conjunction with an effective amount of a different compound which promotes wakefulness.

10. The method of claim 3 comprising administering to the subject the OX2R agonist in conjunction with an effective amount of a different compound which promotes wakefulness.

11. The method of claim 4 comprising administering to the subject the OX2R agonist in conjunction with an effective amount of a different compound which promotes wakefulness.

12. The method of claim 5 comprising administering to the subject the OX2R agonist in conjunction with an effective amount of a different compound which promotes wakefulness.

13. The method of claim 6 comprising administering to the subject the OX2R agonist in conjunction with an effective amount of a different compound which promotes wakefulness.

14. The method of claim 1 comprising administering to the subject the OX2R agonist in unit dosage form, and comprising the antecedent step of removing a capsule or tablet comprising the unit dosage form from a multipack adapted for sequential use.

15. The method of claim 2 comprising administering to the subject the OX2R agonist in unit dosage form, and comprising the antecedent step of removing a capsule or tablet comprising the unit dosage form from a multipack adapted for sequential use.

16. The method of claim 3 comprising administering to the subject the OX2R agonist in unit dosage form, and comprising the antecedent step of removing a capsule or tablet comprising the unit dosage form from a multipack adapted for sequential use.

17. The method of claim 1, wherein the agonist is of formula:

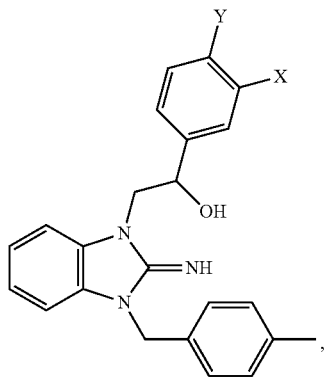

wherein:
X is Cl and Y is H.

18. The method of claim 1, wherein the agonist is of formula:

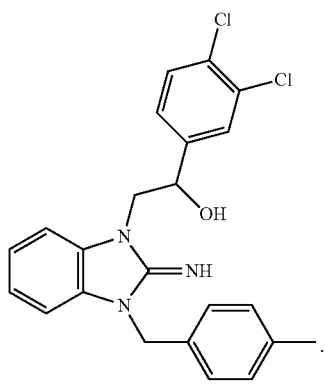

wherein:
X is H and Y is H.

19. The method of claim 1, wherein the agonist is of formula:

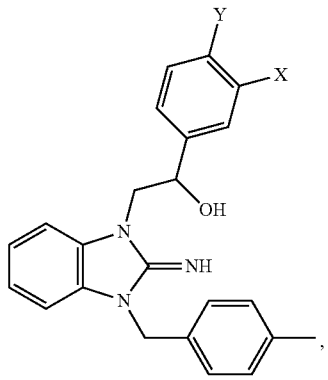

wherein:
X is OMe and Y is H.

20. The method of claim 1, wherein the agonist is of formula:

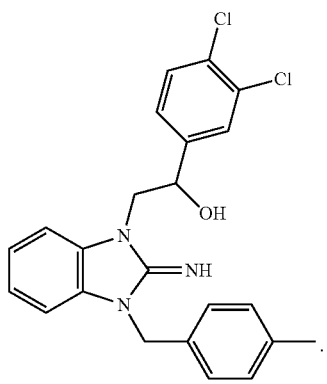

wherein:
X is H and Y is Br.

21. The method of claim 1, wherein the agonist is of formula:

wherein:
X is H and Y is NO$_2$.

22. The method of claim 1 comprising administering to the subject the OX2R agonist in conjunction with an effective amount of a different compound which promotes wakefulness, wherein the compound is caffeine.

23. The method of claim 3 comprising administering to the subject the OX2R agonist in conjunction with an effective amount of a different compound which promotes wakefulness, wherein the compound is caffeine.

24. The method of claim 1 further comprising the antecedent step of determining that the person is in need of said enhanced wakefulness.

25. The method of claim 3 further comprising the antecedent step of determining that the person is in need of said enhanced wakefulness.

26. The method of claim 1 wherein said person subject is determined to afflicted with daytime sleepiness.

27. The method of claim 1 wherein said person subject is determined to afflicted with nighttime insomnia.

28. The method of claim 1 wherein said person subject is determined to afflicted with depression with hypersomnia.

29. The method of claim 3 wherein said person subject is determined to afflicted with daytime sleepiness.

30. The method of claim 3 wherein said person subject is determined to afflicted with nighttime insomnia.

31. The method of claim 3 wherein said person subject is determined to afflicted with depression with hypersomnia.

* * * * *

UNITED STATES PATENT AND TRADEMARK OFFICE
CERTIFICATE OF CORRECTION

PATENT NO. : 8,871,794 B2  
APPLICATION NO. : 13/590064  
DATED : October 28, 2014  
INVENTOR(S) : Yanagisawa et al.

Page 1 of 1

It is certified that error appears in the above-identified patent and that said Letters Patent is hereby corrected as shown below:

On the title page item (75), add --Jeff K. De Brabander, Flower Mound, TX (US), Hidetoshi Kumagai, Tsukuba, JP--

Signed and Sealed this
Twelfth Day of April, 2016

Michelle K. Lee
*Director of the United States Patent and Trademark Office*

UNITED STATES PATENT AND TRADEMARK OFFICE
CERTIFICATE OF CORRECTION

PATENT NO. : 8,871,794 B2
APPLICATION NO. : 13/590064
DATED : October 28, 2014
INVENTOR(S) : Masashi Yanagisawa et al.

Page 1 of 1

It is certified that error appears in the above-identified patent and that said Letters Patent is hereby corrected as shown below:

On the title page, item (75) Inventors, add --Jef K. De Brabander, Flower Mound, TX (US); Hidetoshi Kumagai, Tsukuba (JP)--.

This certificate supersedes the Certificate of Correction issued April 12, 2016.

Signed and Sealed this
Ninth Day of August, 2016

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,871,794 B2 | Page 1 of 1 |
| APPLICATION NO. | : 13/590064 | |
| DATED | : October 28, 2014 | |
| INVENTOR(S) | : Yanagisawa et al. | |

It is certified that error appears in the above-identified patent and that said Letters Patent is hereby corrected as shown below:

On the title page

Item (12) should read Yanagisawa et al.

Item (75) add --Jeff K. De Brabander, Flower Mound, TX (US), Hidetoshi Kumagai, Tsukuba, JP--

This certificate supersedes the Certificate of Correction issued April 12, 2016.

Signed and Sealed this
Thirteenth Day of December, 2016

Michelle K. Lee
*Director of the United States Patent and Trademark Office*